United States Patent
Terentiev

(10) Patent No.: US 7,267,479 B2
(45) Date of Patent: Sep. 11, 2007

(54) MAGNETIC COUPLER FOR HOLDING A MAGNETIC PUMPING OR MIXING ELEMENT IN A VESSEL

(75) Inventor: Alexandre N. Terentiev, Lexington, KY (US)

(73) Assignee: LevTech, Inc., Lexington, KY (US)

( * ) Notice: Subject to any disclaimer, the term of this patent is extended or adjusted under 35 U.S.C. 154(b) by 0 days.

(21) Appl. No.: 11/113,677

(22) Filed: Apr. 25, 2005

(65) Prior Publication Data

US 2005/0201201 A1    Sep. 15, 2005

Related U.S. Application Data

(63) Continuation of application No. 09/724,815, filed on Nov. 28, 2000, now Pat. No. 6,758,593.

(51) Int. Cl.
*B01F 13/08* (2006.01)

(52) U.S. Cl. .................. 366/273; 366/331; 366/343; 366/349

(58) Field of Classification Search ............... 366/273, 366/274, 343, 342, 331, 349; 24/303
See application file for complete search history.

(56) References Cited

U.S. PATENT DOCUMENTS

| | | | | | |
|---|---|---|---|---|---|
| 2,184,152 | A | * | 12/1939 | Saffir | .................. 206/222 |
| 2,693,654 | A | * | 11/1954 | Clark | ..................... 40/1.5 |
| 3,172,645 | A | * | 3/1965 | Price, Jr. | .................. 366/273 |
| 3,497,846 | A | * | 2/1970 | Keller | .................... 335/296 |
| 3,518,884 | A | * | 7/1970 | Wood, Jr. | ............... 374/189 |
| 3,647,397 | A | * | 3/1972 | Coleman | ................ 366/167.1 |
| 3,985,649 | A | * | 10/1976 | Eddelman | ................ 210/695 |
| 4,062,652 | A | * | 12/1977 | Rolfo-Fontana | ........... 422/61 |
| 4,214,874 | A | * | 7/1980 | White | ..................... 73/864.01 |
| 4,642,257 | A | * | 2/1987 | Chase | ....................... 428/63 |
| 4,736,494 | A | * | 4/1988 | Marchesi | ..................... 24/303 |
| 5,120,135 | A | * | 6/1992 | Ullman | ..................... 366/273 |
| 5,207,320 | A | * | 5/1993 | Allen | ......................... 206/220 |
| 5,352,036 | A | * | 10/1994 | Haber et al. | ............... 366/130 |
| 5,527,295 | A | * | 6/1996 | Wing | ........................ 604/254 |
| 5,533,804 | A | * | 7/1996 | Larsson et al. | ............ 366/274 |
| 6,477,749 | B1 | * | 11/2002 | Reiter | ........................ 24/303 |
| 6,908,223 | B2 | | 6/2005 | Bibbo | |
| 2003/0198406 | A1 | | 10/2003 | Bibbo et al. | |
| 2003/0226857 | A1 | | 12/2003 | Bibbo et al. | |
| 2004/0027912 | A1 | | 2/2004 | Bibbo et al. | |
| 2004/0047232 | A1 | | 3/2004 | Terentiev | |
| 2004/0190372 | A1 | | 9/2004 | Goodwin et al. | |
| 2005/0002274 | A1 | | 1/2005 | Terentiev | |

OTHER PUBLICATIONS http://www.csd.uwo.cal/Infoxom/Samples/moonmist.html , "Moonmist Transcript", 5 pages, retrived Aug. 29, 2006.*

* cited by examiner

*Primary Examiner*—Tony G. Soohoo
(74) *Attorney, Agent, or Firm*—King & Schuckli, PLLC

(57) ABSTRACT

A kit for assisting in the set-up of a fluid pumping or mixing system including a superconducting element capable of reaching a transition temperature during a field cooling process is disclosed. In one embodiment, the kit comprises at least one pumping or mixing element including a levitation magnet and at least one charging magnet substantially corresponding in size, shape, and magnetic field distribution to the levitation magnet. The presence of the charging magnet adjacent the superconducting element during the field cooling process enables stable levitation of the pumping or mixing element, including when in a fluid-filled vessel positioned adjacent the superconducting element.

20 Claims, 17 Drawing Sheets

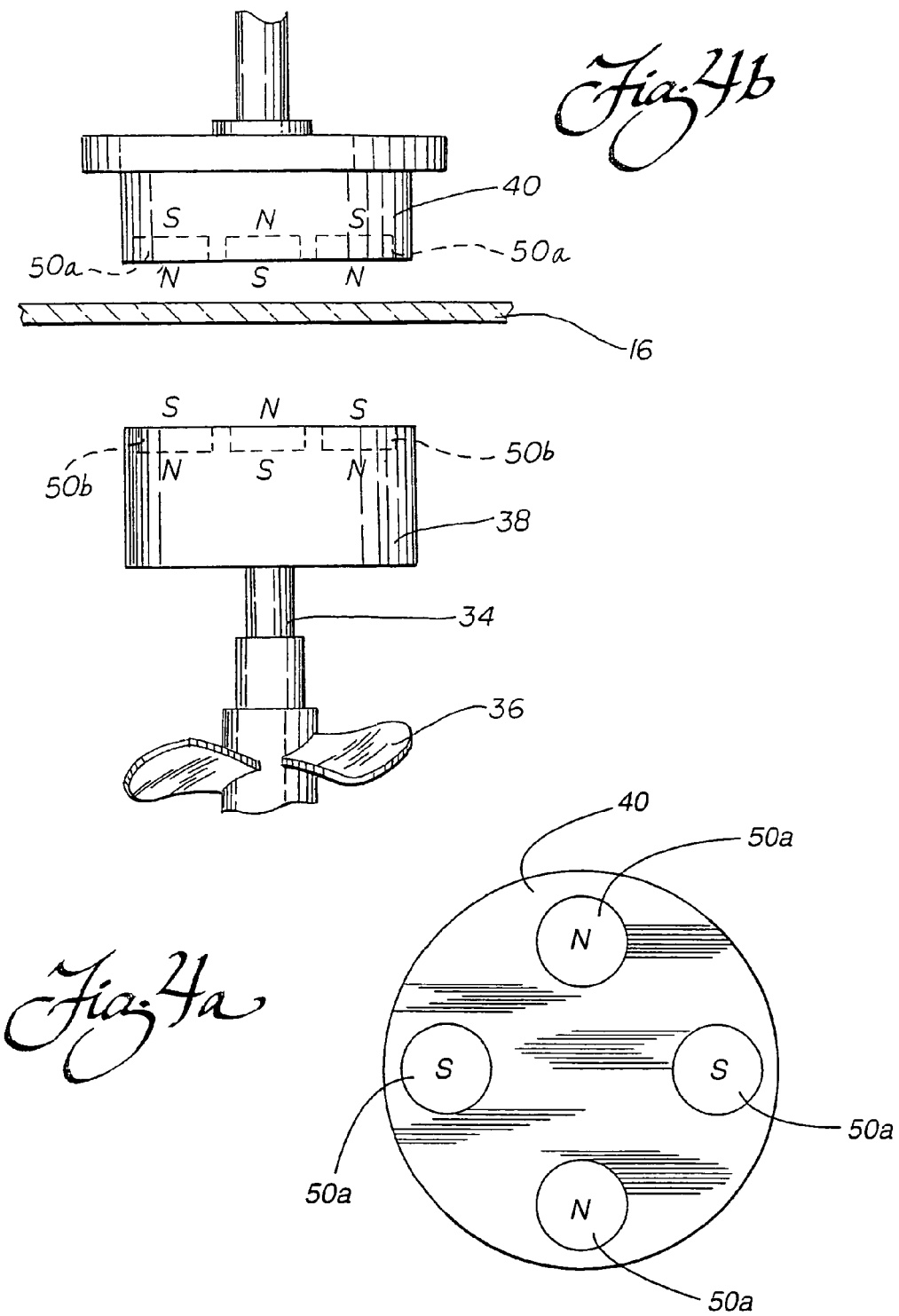

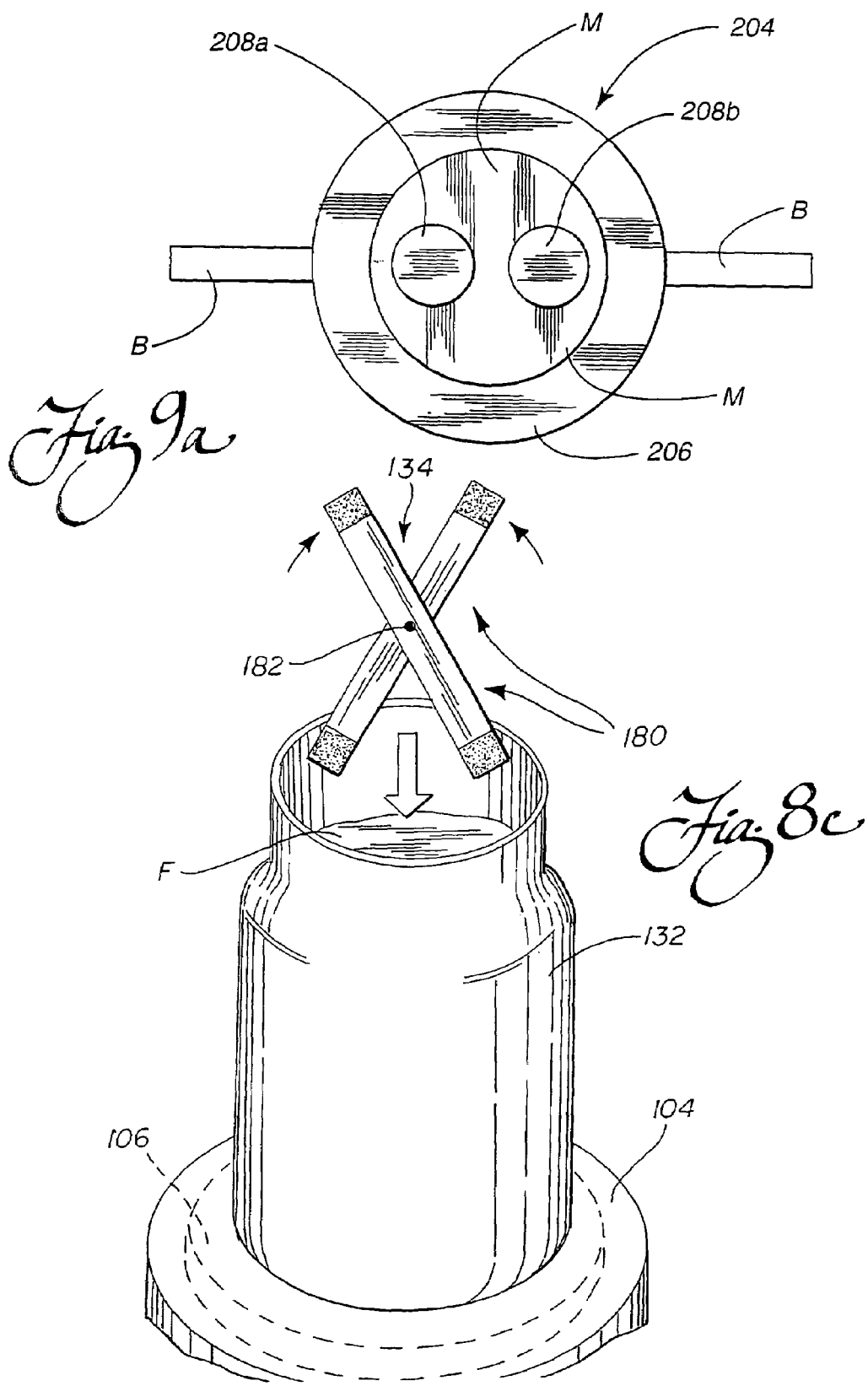

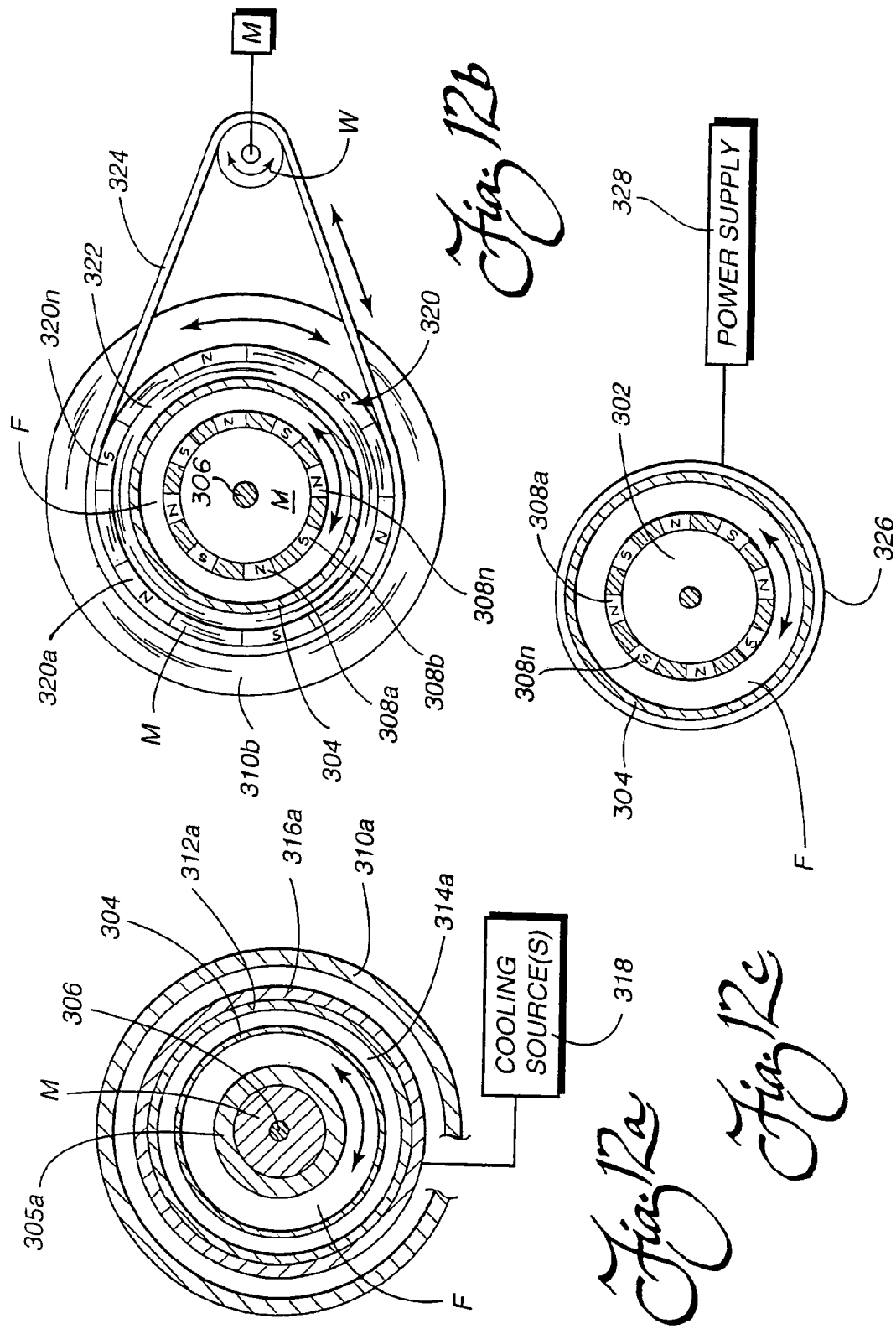

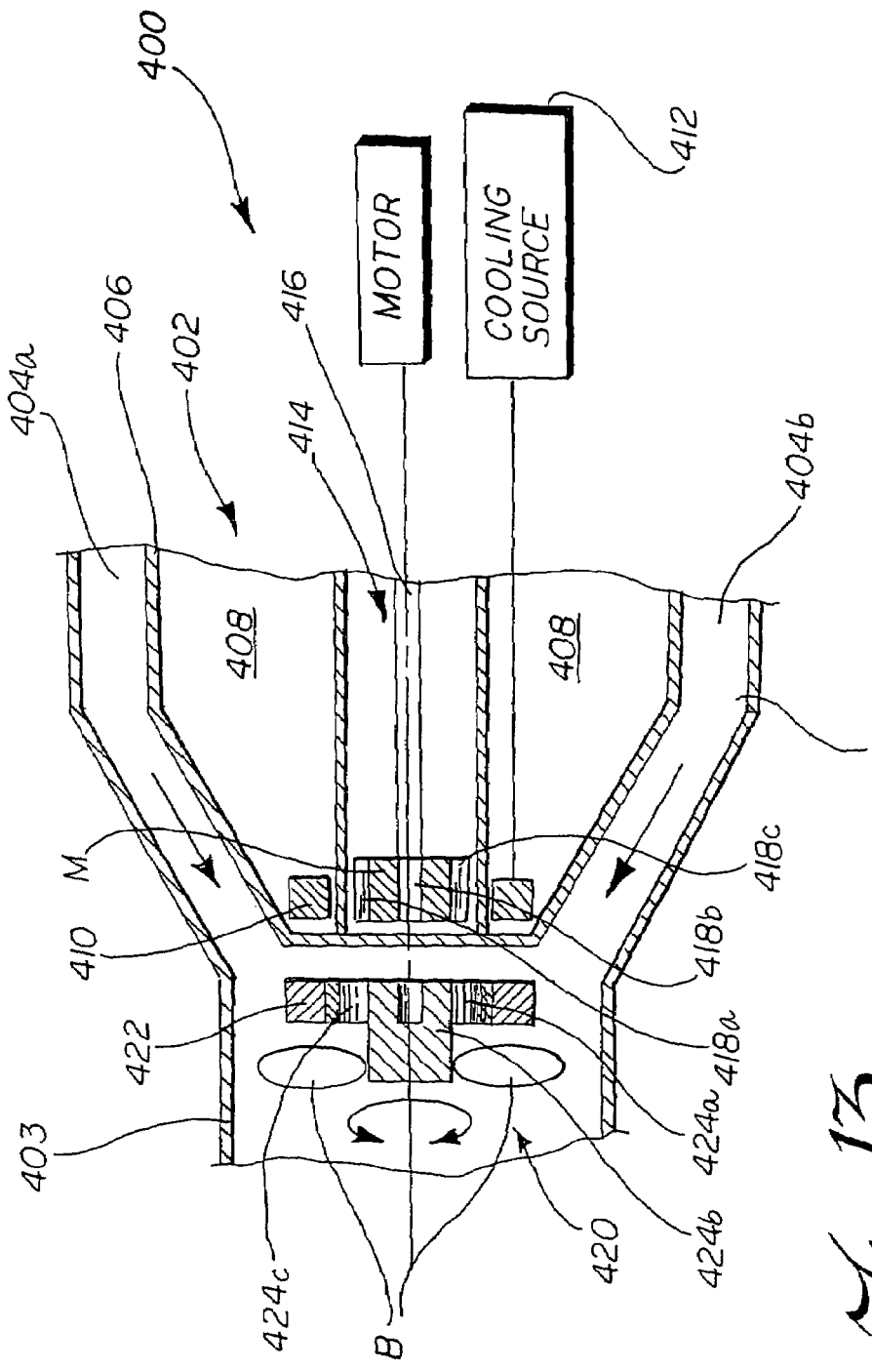

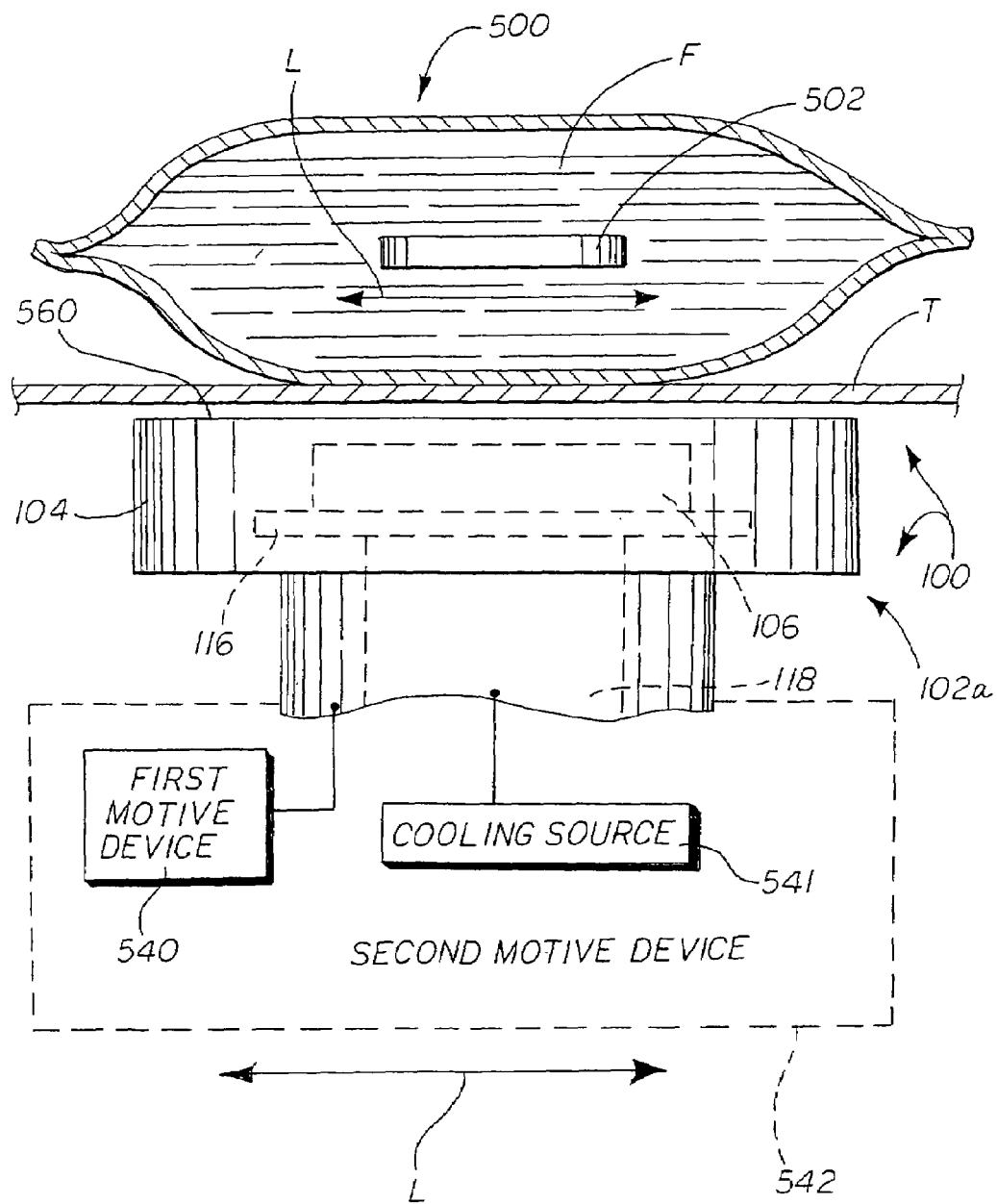

MAGNETIC COUPLER FOR HOLDING A MAGNETIC PUMPING OR MIXING ELEMENT IN A VESSEL

This application is a continuation of U.S. patent application Ser. No. 10/863,910 now U.S. Pat. No. 6,899,454, which is a divisional of U.S. Patent Application Ser. No. 09/724,815, now U.S. Pat. No. 6,758,593.

TECHNICAL FIELD

The present invention relates generally to the mixing or pumping of fluids or the like and, more particularly, to a number of systems, related components, and related methods for pumping or mixing fluids using a rotating magnetic bearing levitated by a superconducting element.

BACKGROUND OF THE INVENTION

Most pharmaceutical solutions and suspensions manufactured on an industrial scale require highly controlled, thorough mixing to achieve a satisfactory yield and to ensure a uniform distribution of ingredients in the final product. Agitator tanks are frequently used to complete the mixing process, but a better degree of mixing is normally achieved by using a mechanical stirrer or impeller (e.g., a set of mixing blades attached to a metal rod). Typically, the mechanical stirrer or impeller is simply lowered into the fluid through an opening in the top of the vessel and rotated by an external motor to create the desired mixing action.

One significant limitation or shortcoming of such an arrangement is the danger of contamination or leakage during mixing. The rod carrying the mixing blades or impeller is typically introduced into the vessel through a dynamic seal or bearing. This opening provides an opportunity for bacteria or other contaminants to enter, which of course can lead to the degradation of the product. A corresponding danger of environmental contamination exists in applications involving hazardous or toxic fluids, or suspensions of pathogenic organisms, since dynamic seals or bearings are prone to leakage. Cleanup and sterilization are also made difficult by the dynamic bearings or seals, since these structures typically include folds and crevices that are difficult to reach. Since these problems are faced by all manufacturers of sterile solutions, pharmaceuticals, or the like, the U.S. Food and Drug Administration (FDA) has consequently promulgated strict processing requirements for such fluids, and especially those slated for intravenous use.

Recently, there has also been an extraordinary increase in the use of biosynthetic pathways in the production of pharmaceutical materials, but problems plague those involved in this rapidly advancing industry. The primary problem is that suspensions of genetically altered bacterial cells frequently used to produce protein pharmaceuticals (insulin is a well-known example) require gentle mixing to circulate nutrients. If overly vigorous mixing or contact between the impeller and the vessel wall occurs, the resultant forces and shear stresses may damage or destroy a significant fraction of the cells, as well as protein molecules that are sensitive to shear stresses. This not only reduces the beneficial yield of the process, but also creates deleterious debris in the fluid suspension that requires further processing to remove.

In an effort to overcome this problem, others have proposed alternative mixing technologies. The most common proposal for stirring fluids under sterile conditions is to use a rotating, permanent magnet bar covered by an inert layer of TEFLON, glass, or the like. The magnetic bar is placed on the bottom of the agitator vessel and rotated by a driving magnet positioned external to the vessel. Of course, the use of such an externally driven magnetic bar avoids the need for a dynamic bearing, seal or other opening in the vessel to transfer the rotational force from the driving magnet to the stirring magnet. Therefore, a completely enclosed system is provided. This of course prevents leakage and the potential for contamination created by hazardous materials (e.g., cytotoxic agents, solvents with low flash points, blood products, etc.), eases clean up, and allows for the desirable sterile interior environment to be maintained.

However, several well-recognized drawbacks are associated with this mixing technology, making it unacceptable for use in many applications. For example, the driving magnet produces not only torque on the stirring magnetic bar, but also an attractive axial thrust force tending to drive the bar into contact with the bottom wall of the vessel. This of course generates substantial friction at the interface between the bar and the bottom wall of the vessel. This uncontrolled friction generates unwanted heat and may also introduce an undesirable shear stress in the fluid. Consequently, fragile biological molecules, such as proteins and living cells that are highly sensitive to temperature and shear stress, are easily damaged during the mixing process, and the resultant debris may contaminate the product. Moreover, the magnetic bar stirrer may not generate the level of circulation provided by an impeller, and thus cannot be scaled up to provide effective mixing throughout the entire volume of large agitation tanks of the type preferred in commercial production operations.

In yet another effort to eliminate the need for dynamic bearings or shaft seals, some have proposed mixing vessels having external magnets that remotely couple the mixing impeller to a motor located externally to the vessel. A typical magnetic coupler comprises a drive magnet attached to the motor and a stirring magnet carrying an impeller. Similar to the magnetic bar technology described above, the driver and stirrer magnets are kept in close proximity to ensure that the coupling between the two is strong enough to provide sufficient torque. An example of one such proposal is found in U.S. Pat. No. 5,470,152 to Rains.

As described above, the high torque generated can drive the impeller into the walls of the vessel creating significant friction. By strategically positioning roller bearings inside the vessel, the effects of friction between the impeller and the vessel wall can be substantially reduced. Of course, high stresses at the interfaces between the ball bearings and the vessel wall or impeller result in a grinding of the mixing proteins and living cells, and loss of yield. Further, the bearings may be sensitive to corrosive reactions with water-based solutions and other media and will eventually deteriorate, resulting in frictional losses that slow the impeller, reduce the mixing action, and eventually also lead to undesirable contamination of the product. Bearings also add to the cleanup problems.

In an effort to address and overcome the limitations described above, still others have proposed levitated bearings designed to reduce the deleterious effects of friction resulting from magnetically coupled mixers. By using a specially configured magnetic coupler to maintain only a repulsive levitation force in the vertical direction, the large thrust force between the stirring and driving magnets can be eliminated, along with the resultant shear stress and frictional heating. An example of one such arrangement is shown in U.S. Pat. No. 5,478,149 to Quigg.

However, one limitation remaining from this approach is that only magnet-magnet interactions provide the levitation. This leads to intrinsically unstable systems that produce the desired levitation in the vertical direction, but are unable to control side-to-side movement. As a result, external contact bearings in the form of bearing rings are necessary to laterally stabilize the impeller. Although this "partial" levitation reduces the friction between the impeller and the vessel walls, it does not totally eliminate the drawbacks of the magnetically coupled, roller bearing mixers previously mentioned.

In an effort to eliminate the need for contact or other types of mechanical roller bearings, complex feedback control has been proposed to stabilize the impeller. Typical arrangements use electromagnets positioned alongside the levitating magnet. However, the high power level required to attain only sub-millimeter separations between the levitating magnet and the stabilizing magnets constitutes a major disadvantage of this approach. Furthermore, this solution is quite complex, since the stabilizing magnets must be actively monitored and precisely controlled by complex computer-implemented software routines to achieve even a moderate degree of stability. As a consequence of this complexity and the associated maintenance expense, this ostensible solution has not been accepted in the commercial arena, and it is doubtful that it can be successfully scaled up for use in mixing industrial or commercial scale process volumes.

Still others have proposed the use of superconductive materials to levitate magnetic bearings. Despite recent advances in the art, significant limitation on the application of this technology to mixing systems results from the extraordinarily cold temperatures required to create the desired superconductive effects. Even the recently discovered "high temperature" superconductors require temperatures on the order of 77 to 130 Kelvin to induce reliable, stable levitation in a magnetic bearing. In the past, the relatively wide separation distance required between the bearing, the cryostat outer wall, and the superconducting element necessary to prevent unwanted cooling of the fluid has limited the industrial applicability of this approach. To date, applications of this technology to fluids have been primarily in the pumping of cryogens or the like, such as those typically used in cold fusion experiments, in flywheels or other energy storage devices, or for space travel (see representative U.S. Pat. No. 5,747,426 to Abboud or U.S. Pat. No. 4,365,942 to Schmidt), where there is of course little concern for the inevitable cooling effect created.

In my prior U.S. Pat. No. 5,567,672, I describe levitating a magnet above a superconducting element in a cryostat, which contains the cooling source used to cool the superconducting element. This arrangement could possibly be used as part of a system for mixing temperature sensitive fluids, such as cell suspensions or blood, as disclosed herein. However, the resultant increased separation created by the double wall vacuum gap may decrease the stability and the load capacity of the levitating magnet. This may limit the applications in which this arrangement is useful, and could especially preclude use with particularly viscous fluids or with the large volumes of fluid typically present in commercial scale operations.

Thus, a need is identified for an improved system having a levitating magnetic bearing for mixing or pumping fluids, and especially ultra-pure, hazardous, or delicate fluid solutions or suspensions. The system would preferably employ a magnetic bearing that levitates in a stable fashion to avoid contact with the bottom or side walls of the vessel. Since the bearing would levitate in the fluid, no mixing rod or other structure penetrating the mixing vessel would be necessary, thus eliminating the need for dynamic bearings or seals and all potentially deleterious effects associated therewith. Since penetration is unnecessary, the vessel could be completely sealed prior to mixing to avoid the potential for contamination and reduce the chance for exposure in the case of hazardous or biological fluids, such as contaminated blood or the like. The vessel and magnetic bearing could also be made of disposable materials and discarded after each use, which would eliminate the need for cleaning or sterilization. The absence of a mixing or stirring rod penetrating through the vessel would also allow a slowly rotating impeller to be held at an off-axis position in a sealed vessel, thus making it possible to independently rotate the vessel about its central axis to achieve very gentle, yet thorough, mixing.

In the case of warm or temperature-sensitive fluids, the use of superconductivity to provide the desired levitation would be possible by thermally isolating and separating the superconducting element from the magnetic bearing and providing a separate, substantially isolated cooling source. This combined thermal isolation and separation would avoid creating any significant cooling in the vessel, the magnetic bearing or the fluid being mixed or pumped. The use of a superconductor would also eliminate the sole reliance on magnet-magnet repulsion to provide the levitation force and the concomitant need for active electronic control systems to ensure stable levitation. Overall, the proposed system would have superior characteristics over existing mixing or pumping technologies, especially in terms of sterility, mixing quality, safety and reliability, and would be readily adaptable for use in larger, industrial scale operations.

SUMMARY OF THE INVENTION

To meet these needs, and in accordance with a first aspect of the present invention as described herein, a number of systems that are capable of pumping or mixing fluids, including temperature sensitive fluids, using a magnetic bearing, impeller, rotor or other element or device capable of generating a pumping or mixing action in a fluid (hereinafter generically referred to as a "magnetic bearing') levitated by a superconducting element are disclosed. The magnetic bearing may be placed in a vessel positioned adjacent to the wall of a cryostat or other housing for the superconducting element. A separate cooling source thermally linked to the superconducting element provides the necessary cooling to create the desired superconductive effects and induce levitation in the magnetic bearing. The cryostat outer wall or other housing may define a chamber around the superconducting element. This chamber thermally isolates the superconducting element from the vessel containing the bearing. To minimize thermal transfer from the superconducting element to the outer wall or housing, this chamber is preferably evacuated, but may be instead filled with an insulating material. This thermal isolation and separation means that the superconducting element may be placed in close proximity to the outer wall of the cryostat or other housing adjacent to the vessel to achieve a significant reduction in the separation distance between the levitating bearing and the superconducting element. This advantageously enhances the magnetic stiffness and loading capacity of the bearing as it levitates. However, since the superconducting element may be thermally isolated from the wall or housing, the magnetic bearing, and hence the vessel and fluid contained therein, are not exposed to the cold temperatures required to generate the desired superconductive effects. By using means external to the vessel to rotate one of the levitating magnetic bearing or the superconducting element, the desired pumping or mixing action is provided.

As should be appreciated from reviewing the foregoing description, several advantages may possibly be provided through the use of the mixing or pumping system of the present invention, depending in part upon the particular application. Since the rotating magnetic bearing levitates in the fluid, there is no mechanical stirrer or mixing rod extending through any wall of the vessel, which means that the vessel can be completely sealed from the outside environment, if desired. This eliminates the need for a dynamic bearing or seal and the concomitant problems with leakage, sterility, and the like, which makes the present arrangement particularly well suited for use in pumping or mixing ultra-pure or hazardous fluids. Furthermore, exceptionally stable levitation of the magnetic bearing is provided by the minimal separation distance between the superconducting element and the magnetic bearing. Due to the thermal isolation and separation of the superconducting element from the cryostat wall, the system may even be used to pump or mix temperature sensitive fluids. In any case, contact-free, stable levitation reduces the incidence of frictional heating or unwanted shear stresses, both of which can have a significant deleterious effect on sensitive fluids, such as cell suspensions or the like.

In one possible embodiment, the magnetic bearing includes first and second spaced permanent magnets, which may be mounted at the opposite ends of a support shaft. The first magnet is placed in the fluid vessel closest to the outer wall of the cryostat such that it is levitated by the superconducting element. While those of skill in the art will understand that the polarity of the first permanent magnet is not critical for producing the desired levitation, it is preferred that it is disk-shaped and polarized in the vertical direction. This ensures that the magnetic field generated is substantially symmetrical and the desired stable levitation and free rotation relative to the vertical axis results.

The second permanent magnet forms a magnetic coupling with the motive device for rotating the magnetic bearing, which is preferably a drive magnet coupled to the rotating shaft of a motor. In applications where the stability of the magnetic bearing is particularly important, the drive magnet includes more than one magnet, and in the one embodiment has at least two sub-magnets that correspond to opposite polarity sub-magnets forming a part of the second permanent magnet. In addition to creating the desired magnetic coupling for transmitting the driving torque, these cooperating sub-magnets produce an attractive force that balances with the levitational force provided by the superconducting element to keep the bearing properly balanced in the vertical direction. The cooperating sub-magnet pairs also keep the levitating bearing axially aligned and prevent side-to-side movement without the need for active control. In combination, the magnetic couplings created by the sub-magnet pairs allow the bearing to rotate in an exceptionally stable fashion. This reduces the chances of the bearing inadvertently contacting between the bottom and side walls of the vessel, and eliminates the need for electromagnets, roller bearings, or like structures found in prior art pumps or mixers.

In an alternate version of the magnetic bearing, at least one, and preferably a plurality of chambers are provided for holding a gas or other substance that is lighter than the fluid or other substance surrounding the bearing. These chambers serve to assist in levitating the magnetic bearing in the fluid, while the pinning forces created by the superconducting element simultaneously assist in keeping the magnetic bearing properly positioned at the desired location in the vessel. The chamber or chambers thus effectively reduce the amount of levitation force that must be supplied by the superconducting element.

The superconducting element may be formed of melt-textured Yttrium-Barium Copper Oxide (YBCO), which is a well-known high temperature, or "Type II," superconducting material, formed into a relatively thin pellet. The thermal link between the superconducting element and the cooling source is created by an elongate rod formed of a material having desirable thermal transfer characteristics. Metals, such as copper, brass, aluminum, or the like, are particularly well-suited for this purpose, but the use of any other material having good thermal conductance/low thermal resistance is possible. The rod may be cylindrical in shape such that one end has a relatively large surface area that fully contacts and engages an entire face of the superconducting element to maximize thermal transfer while one end of the rod supports the superconducting element in the chamber defined by the outer wall of the cryostat or other housing, which remains at room temperature, the opposite end is kept in thermal contact with the cooling source. The cooling source may take the form of a separate cooling chamber in the cryostat holding a cryogen at a temperature between 4.2 and 130 Kelvin, and most preferably liquid nitrogen at a temperature between approximately 65-80 Kelvin. Instead of liquid cryogens, the use of alternate means for cooling the rod is possible, such as providing a separate closed cycle refrigerator that is kept entirely outside of the cryostat or other housing for the superconducting element.

Since the magnetic bearing levitates without the need for a mixing rod or other form of driving shaft, it should be appreciated that the vessel containing the fluid may be completely sealed from the outside environment and used to mix, rather than pump, the fluid. By using such an arrangement, the potential for leakage or contamination during mixing is eliminated, as is the risk of exposing hazardous or biologically active fluids to the environment. Forming the sealed vessel and the magnetic bearing from disposable materials is also possible, such that both can simply be discarded after mixing is complete and the fluid is retrieved or recovered, if necessary. This advantageously avoids the need for clean up or sterilization of the vessel and bearing.

Also, since there is no need for a dynamic bearing or seal for any drive shaft penetrating through a wall of the vessel, the vertical center axis of rotation of the magnetic bearing can be easily offset from the vertical center axis of the vessel. The vessel can then be rotated in a direction counterclockwise to the rotation of the bearing mounted in such an offset position. By doing so, gentle, yet thorough mixing may be provided in an efficient manner.

It should also be appreciated that other alternatives to a sealed vessel are possible. Of course, the vessel may simply be open to the ambient environment, as may be desired during the mixing of some solutions or suspensions that require exposure to open air to achieve a desired result. Alternatively, the vessel may be substantially sealed with only an inlet and an outlet, such that the rotating magnetic bearing/impeller provides pumping action to move the fluid through the vessel. Manufacturing the open top or substantially sealed vessel of disposable materials is also possible, such that both the vessel and magnetic bearing can simply be discarded after use to avoid the need for clean up or sterilization. The vessel can also be a flexible bag or other non-rigid type of container, the dimensions of which are essentially defined by the volume of fluid held therein.

As should further be appreciated, the system described above is based on the use of a stationary superconducting element and a magnetic bearing that includes a levitation magnet and separate "driven" magnets. The driving force is applied to the driven magnets from adjacent the top of the vessel, while the levitation force is provided by the other, levitating magnet adjacent to the bottom of the vessel. While this system provides the several advantages described above, in many practical applications, it is advantageous to keep the top of the mixing vessel or pumping head substantially clear from obstructions. For instance, if the mixing vessel includes a number of different ports and connections on the top, such as a filling port, temperature sensor connector, pH sensor connector, or the like, driving the levitating magnetic bearing from the top may interfere with these structures, thus possibly making operation somewhat inconvenient. This is also true in the case where the levitating magnetic bearing is used in a pumping chamber or centrifugal pumping head, where it is often desirable to place the fluid inlet in the top or upper wall of the vessel.

Moreover, in case of accidental decoupling of the driving magnet with the driven magnet at the opposite side of the levitating magnetic bearing, the shaft may lose vertical stability and fall into contact with the bottom or sides of the container. If this occurs, it is impossible to recover the stable levitation without opening the container, if sealed, or otherwise disturbing the fluid. This, of course, can lead to deleterious contamination. Yet another reason for providing an alternative to the top driven arrangement is that it eliminates the need for a fixed height vessel or container for holding the fluid. For example, in the case of where the vessel is in the form of a flexible bag, the vertical dimension of the bag often depends on the amount of fluid present, as well as the size and overall geometry of the bag itself. By magnetically driving a low-profile, levitating bearing or impeller in a stable, non-contact fashion from only the bottom of such a flexible plastic container, it could be of a reduced vertical dimension without compromising the degree of pumping or mixing action created.

Driving and levitating a magnetic bearing from the same side of the vessel also reduces the number of permanent magnets required. This is because the levitation magnets may simultaneously serve as the "driven" magnets. Eliminating the total number of magnets required not only reduces the materials cost, but also creates a bearing that is less complicated to manufacture.

Thus, another purpose of the present invention is to provide a magnetic bearing, and most preferably a low-profile, disk-shaped magnetic bearing or impeller (with or without blades, vanes, or the like) that is both levitated by a superconducting element and magnetically driven by means located outside of the vessel, and preferably on the same side of the vessel as the superconducting element. The magnetic bearing can thus be used for mixing or pumping fluids in a variety of vessels without regard to height, including flexible containers, such as bags or the like. Also, as described above, the magnetic bearing can be used along with a disposable plastic container (or with disposable impeller blades along with a disposable plastic pumping chamber or head).

To achieve this second goal, another version of a pumping or mixing system using a levitating magnetic bearing is disclosed. In this version, the thermally isolated superconducting element is contained within a wall defining a chamber that may be evacuated or insulated to create the desired thermal separation, as above, but instead of rotating the magnetic bearing including separate drive magnets, the motive device rotates both the wall and the superconducting element together. Accordingly, both the levitation and motive forces for the magnetic bearing are supplied by the same superconducting element (which actually can be formed of several component parts). To ensure proper rotation of the bearing, it includes at least two permanent magnets having different polarities that together create a non-symmetrical magnetic field with respect to the axis of rotation of the superconducting element. The bearing may also carry one or more blades or vanes to enhance the mixing or pumping action. In an alternate version of this embodiment, the cooling source may also be rotated along with the wall creating the chamber for thermally isolating the superconducting element (or may serve to couple the chamber to the motive device). In either case, the low-profile, magnet-carrying bearing may thus be efficiently and effectively levitated and rotated from the bottom of a vessel (or pumping chamber/head) resting on a stable support structure, while at all times remaining thermally separated and isolated from the cold superconducting element.

When using a vessel having a narrow opening, it may be difficult or impossible to insert the typical pancake or disk-shaped magnetic bearing in the fluid. Thus, an alternate version of a magnetic bearing, and one especially adapted for use in the pumping or mixing system of this second embodiment, is disclosed. The magnetic bearing is in the form of a low-profile rod. Each end of the rod carries a magnet. These magnets may serve as both the levitating and the driven magnets in the case where the bearing is positioned above a rotating superconducting element.

In another version, two of the low-profile rods, each carrying at least two magnets having identical polarities, are pinned together, preferably at their centers. The rods are thus capable of rotating relative to each other to form a low-profile magnetic bearing that can easily pass through a narrow opening in a vessel. Since the magnets at the end of each rod have the same polarity, they not only serve to levitate and drive the bearing, but also repel each other to keep the rods from aligning when rotating in the vessel. Instead of or in addition to pinning the rods together, it is also possible to fabricate one or both rods of a flexible material, and possibly a single integral piece of material. As a result of the flexibility, the bearing formed from the rigidly coupled rods can be deformed to pass through any narrow opening in a vessel or container.

Despite the preference for using the system of this second possible embodiment for pumping or mixing temperature sensitive fluids in view of the beneficial nature of the thermal separation, it should be appreciated that it is possible to use it for pumping or mixing non-temperature sensitive or cryogenic fluids as well. For example, the evacuated housing or like chamber surrounding the rotating superconducting element can be eliminated altogether, since there is no need to thermally separate it from the support structure for the vessel containing the magnetic bearing when a cold or non-temperature sensitive fluid is being pumped or mixed. Nevertheless, the desired stable, contact free levitation is still achieved.

In accordance with a third aspect of the present invention, the thermally isolated superconducting element provides the levitation, substantially as described above, while a separate motive device positioned adjacent to the superconducting element serves to rotate the magnetic bearing. In a most preferred version of this embodiment, the superconducting element is annular and positioned in a correspondingly shaped chamber defined by the outer wall of a cryostat or like device. This chamber may be evacuated or insulated to provide the desired thermal separation and isolation for the superconducting element. The wall also defines a bore or opening in the center of the chamber housing the superconducting element for receiving a portion of a motive device, such as a shaft carrying alternating polarity driving magnets at one end. The opposite end of the shaft is coupled to a motor also forming a part of the motive device. The magnetic bearing, in turn, carries a first "levitating" magnet corresponding in shape to the superconducting element, as well as at least two alternating polarity "driven" magnets that couple with the corresponding driving magnets. This magnetic coupling with the driven shaft serves to provide the desired rotation for the levitating bearing, while the superconducting element simultaneously serves to levitate the bearing in the vessel.

To provide the necessary cooling, a thermal link connects the superconducting element with a separate cooling source, such as a container holding a suitable liquid cryogen or a closed-cycle refrigerator. Preferably, like the superconducting element, the rod and cooling source are each held in evacuated or insulated chambers to prevent any thermal transfer to or from the outside environment. In the case of evacuation, all three chambers are preferably in communication, but each may also be kept separate, such as by partitions, and individually evacuated or insulated. Thus, like the second embodiment, this system can also efficiently and effectively rotate a thermally isolated and separated magnetic bearing in a vessel containing a fluid to provide the desired pumping or mixing action. However, it should be appreciated that, like in the second embodiment, thermal separation is not a critical requirement, since the system of this embodiment could also be used to pump or mix non-temperature sensitive or cryogenic fluids as well.

In accordance with a fourth aspect of the invention, the vessel is in the form of a pipe containing a stationary or passing fluid. A correspondingly shaped superconducting element, which is preferably provided in two spaced component parts, surrounds the pipe. Each element is thermally separated and isolated from the outer surface of the pipe, such as by evacuating a chamber defined by a wall surrounding the element or filling it with insulation. A bearing positioned in the pipe carries levitating magnets corresponding in number to the components of the superconducting element and preferably positioned at each end of the bearing to ensure that a stable levitation force is achieved. As described above, the superconducting element may be thermally linked to a separate cooling source, such as a liquid nitrogen container, refrigerator, or the like. This link provides the necessary cooling such that the superconducting element causes the magnetic bearing to levitate in the pipe in a stable and non-contact fashion.

To rotate the bearing, it may also carry a plurality of driven magnets that correspond to driving magnets positioned externally to the vessel and rotated by a motive device. Alternatively, a winding may be provided around the vessel and supplied with an electrical current to create an electric field that induces rotation in the driven magnets carried on or attached to the bearing. In either case, a levitating, rotating magnetic bearing is provided for "inline" use in a pipe or other narrow, elongated vessel.

In an alternate "inline" embodiment, the cryostat or other wall defining a chamber for housing the superconducting element is positioned in the vessel, such that the superconducting element aligns with and corresponds to a levitation magnet in the bearing, while separate, room-temperature driving magnets forming a part of a motive device correspond to and align with opposite polarity driven magnets in the bearing to form a magnetic coupling. The chamber is preferably evacuated or insulated to thermally isolate the superconducting element from the bearing and the surrounding fluid. A separate cooling source is also provided to supply the necessary cooling to the superconducting element to induce levitation in the bearing. The superconducting element and surrounding chamber may both be annular, as in the third embodiment. The inner wall creating this annular chamber also defines a bore for receiving the end of a driven shaft carrying the driving magnets for coupling with the adjacent driven magnets on the bearing. The bearing may also carry one or more blades or vanes to enhance the pumping or mixing action.

In accordance with a fifth aspect of the present invention, an assembly for use in containing a fluid undergoing pumping or mixing is provided. The assembly comprises a vessel formed of a flexible disposable material capable of holding a fluid and a magnetic bearing positioned in the vessel. Thus, when used in conjunction with a pumping or mixing system wherein the magnetic bearing is levitated in the vessel by an adjacent superconducting element, both the vessel and the bearing can be disposed of when the pumping or mixing operation is complete and the fluid is recovered. While not an exhaustive list, the vessel can be selected from the group of an open-top container, a pipe, a container having an inlet for receiving a flow of fluid and an outlet for expelling a flow of fluid, a sealed container, or a flexible bag. An attachment or cover containing a coupler comprised of a ferromagnetic material or the like may also be provided to keep the bearing in the proper position relative to the bag or vessel, such as during shipping or the like.

Ensuring that the magnetic bearing used in each system is both the proper one for that particular system and is sized appropriately may also be important. To do so, and in accordance with a sixth aspect of the invention, it is possible to provide a transmitter in one of the magnetic bearing or the vessel for generating a signal that is received by a receiver positioned elsewhere in the system (or vice versa), such as one positioned adjacent to the superconducting element. A controller for the system, such as a computer, can then be used to maintain the system in a non-operational, or "lockout," condition until such time as the appropriate signal is received.

In accordance with a seventh aspect of the invention, a kit is also provided to assist in the set-up of any of the systems previously described. Specifically, it is necessary during field cooling to cool the superconducting element to below its transition temperature in the presence of a magnetic field in order to induce levitation in a permanent magnet producing the same magnetic field. This cooling process causes the superconducting element to "remember" the magnetic field, and thus produce the desired stable and reliable levitation each time a similar field is present. While it is possible to use the magnetic bearing to produce the magnetic field during field cooling, oftentimes the bearing will be pre-sealed in the vessel or container. This makes it difficult, if not impossible, to ensure that the magnet is properly aligned and spaced from the superconducting element during field cooling.

To overcome this problem, the kit of the present invention comprises at least one charging magnet having a size, shape, and magnetic field distribution identical to the levitation magnet contained in the particular bearing slated for use in one of the pumping or mixing systems previously described. The charging magnet is placed adjacent to the superconducting element during cooling, such as on the upper surface of the cryostat or other chamber surrounding the superconducting element (or a stable support structure for the bearing). Once cooling below the transition temperature is complete, the charging magnet may be removed and replaced with the vessel containing the corresponding magnetic bearing.

The kit or charging magnet may also comprise a spacer. This spacer allows the charging magnet to simulate the spacing of the magnetic bearing above the superconducting element to ensure that the desired levitation height is achieved once the vessel containing the actual bearing to be levitated is in position. The spacer is fabricated of a non-magnetic material to avoid interfering with the charging process. By also providing a variety of different sizes, shapes, and configurations of charging magnets (e.g., annular magnets), it is possible to easily perform field cooling for any size or shape of levitation magnet in the corresponding magnetic bearing.

During field cooling, and regardless of whether the magnetic bearing or a separate charging magnet is used to produce the charging magnetic field, it is possible to induce an undesired magnetic state in the superconducting element, such as if the position of the bearing or charging magnet is not correct during cooling. Since improper charging may prevent the magnetic bearing from levitating in a stable fashion, "recharging" the superconducting element may be required.

In accordance with an eighth aspect of the present invention, a heater may be provided adjacent to the superconducting element for use in facilitating recharging. More specifically, by activating this heater, the superconducting element may be quickly brought up from the transition temperature for recharging. Once the position of the bearing or charging magnet is adjusted or corrected, the heater may be turned off and the superconducting element once again allowed to cool to the transition temperature in the presence of the desired magnetic field. Of course, this operation may be repeated as necessary until the desired stable levitation is achieved.

In many of the above-described embodiments, the pumping or mixing action is essentially localized in nature, since the bearing is rotated on a fixed axis relative to the vessel. This maybe be undesirable in some situations, such as where the vessel is relatively large, as compared to the magnetic bearing. Thus, in accordance with a ninth aspect of the invention, the particular system used to supply the pumping or mixing action may be provided with a motive device for physically moving the superconducting element (which may also be simultaneously rotated). Moving the superconducting element relative to the vessel will cause the levitating magnetic bearing to follow a similar path.

In accordance with a tenth aspect of the present invention, a method of levitating and rotating a magnetic bearing, such as for pumping or mixing a fluid in a vessel, is disclosed. The method includes the steps of placing a magnetic bearing in the vessel. Levitation is induced in the magnetic bearing by a superconducting element, which may be positioned in an insulated or evacuated chamber defined by the outer wall of a cryostat or other housing. If present, the chamber serves to thermally isolate and separate the vessel, fluid, and magnetic bearing from the superconducting element, which is thermally linked to a separate cooling source. Upon rotating one of the levitating magnetic bearing or the superconducting element in the vessel, the desired mixing or pumping action is provided. As described above, the magnetic bearing and vessel may also be formed of disposable materials and discarded once mixing is complete and the fluid is recovered. Other methods are also disclosed for accomplishing the goals of the other embodiments previously described.

BRIEF DESCRIPTION OF THE DRAWINGS

The accompanying drawings incorporated in and forming a part of the specification illustrate several aspects of the present invention and, together with the description, assist in explaining the principles of the invention. In the drawings:

FIG. 4a is a bottom view of the drive magnet used in situations where exceptional rotational stability of the magnetic bearing of the preferred embodiment is required;

FIG. 4b is a partially cross-sectional, partially cutaway side view of the system showing the drive magnet of FIG. 4a magnetically coupled to a similarly constructed second permanent magnet forming a part of the magnetic bearing;

FIG. 8c illustrates the magnetic bearing of FIG. 8b in a partially folded state for insertion in the narrow opening of a vessel or container;

FIG. 9a is a top or bottom view of one possible embodiment of a magnetic bearing for use in the system of FIG. 9;

FIG. 12a is a cross-sectional view taken along line 12a-12a of FIG. 12;

FIG. 12b is a cross-sectional view taken along line 12b-12b of FIG. 12;

FIG. 12c is a cross-sectional view of the embodiment of FIG. 12, but wherein the motive device is in the form of a winding around the vessel for receiving an electrical current that creates an electrical field and causes the magnetic bearing to rotate;

FIG. 13 is an alternate embodiment of an inline levitating magnetic bearing, similar in some respects to the embodiment of FIG. 9;

FIG. 14b is an enlarged, partially cross-sectional, partially cutaway side view showing the use of a second motive device in the system of FIG. 14, such as a linear motion device, for moving the superconducting element, and hence, the magnetic bearing to and from inside of the vessel;

DETAILED DESCRIPTION OF THE INVENTION

Figure 1:
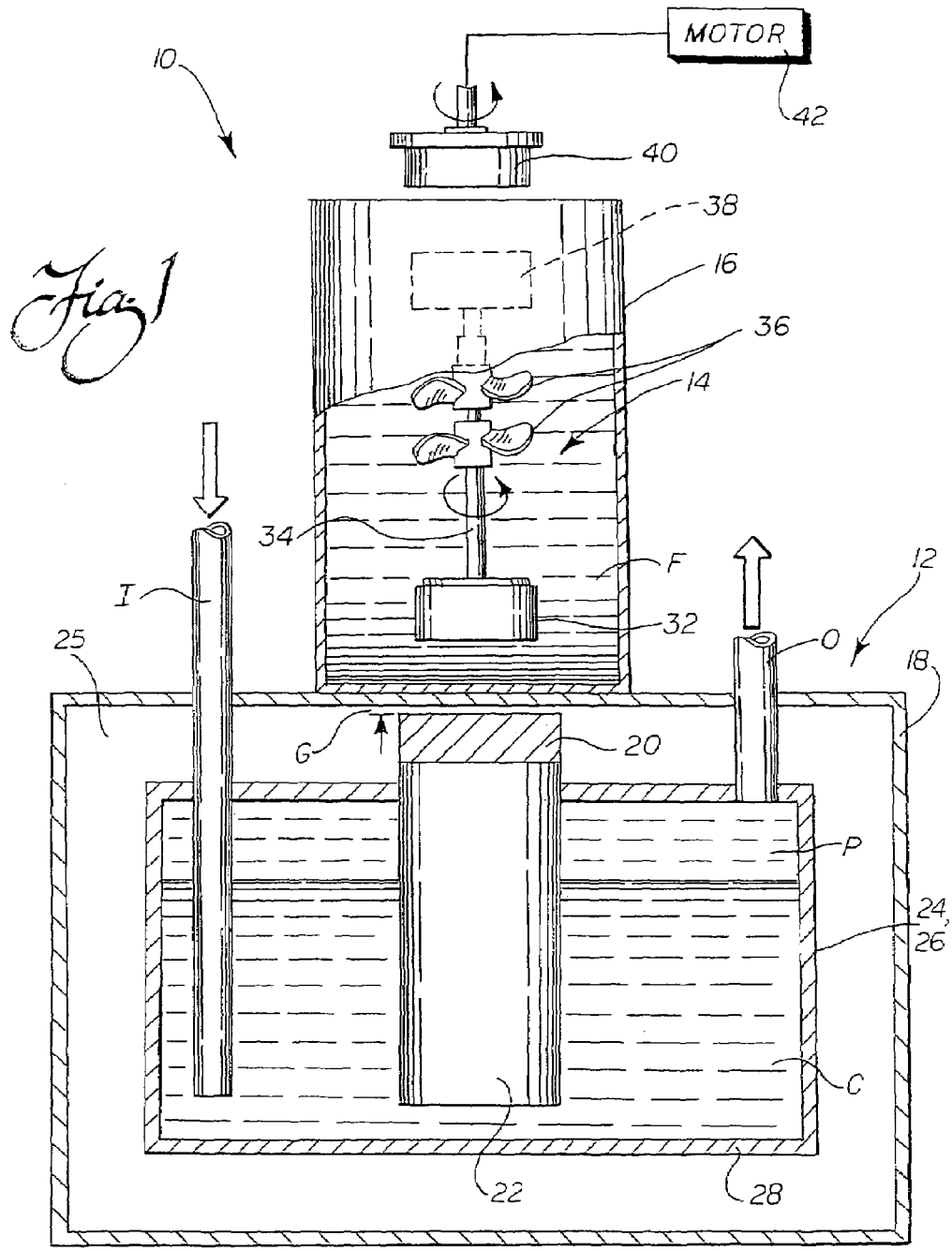
FIG. 1 is a partially cross-sectional, partially cutaway, partially schematic view of one embodiment of the system of the present invention wherein the levitating magnetic bearing is rotated by an external drive or driving magnet to mix a fluid in a vessel and the cooling source is a separate cooling chamber defined by the outer wall of a cryostat holding a cryogen.

Reference is now made to FIG. 1, which shows a first possible embodiment of the mixing or pumping system 10 of the present invention. In this embodiment, a cryostat 12 is used to hold the cooling source for the superconducting element that produces the desired levitation in a pumping or mixing element or device, which as shown in the form of a magnetic bearing 14. The bearing 14 is placed in a vessel 16 positioned external to the cryostat 12, which may already contain a fluid F or may be filled after the bearing is in place. It should be appreciated at the outset that the term "fluid" is used herein to denote any substance that is capable of flowing, as may include fluid suspensions, gases, gaseous suspensions, or the like, without limitation. The vessel 16 for holding the fluid is shown as being cylindrical in shape and may have an open top. Alternatively, it may be completely sealed from the ambient environment to avoid the potential for fluid contamination or leakage during mixing, or adapted to pump the fluid F from an inlet to an outlet in the vessel 16 (see FIG. 2). In any case, the vessel 16 may be fabricated of any material suitable for containing fluids, including glass, plastic, metal, or the like. Of course, the use of lightweight plastic or other high density polymers is particularly desirable if the vessel 16 is going to be discarded after mixing or pumping is complete, as set forth in more detail in the description that follows.

As illustrated in FIG. 1, the vessel 16 rests atop the outer wall 18 of the cryostat 12. Preferably, this outer wall 18 is fabricated of non-magnetic stainless steel, but the use of other materials is of course possible, as long as the ability of the magnetic bearing 14 to levitate and rotate remains substantially unaffected. Positioned inside of and juxtaposed to this wall 18 is a superconducting element 20. The superconducting element 20 is supported by a rod 22 that serves as the thermal link between the superconducting element 20 and a separate cooling source 24. The outer wall 18 of the cryostat 12 defines a chamber 25 that is preferably evacuated to thermally isolate the cold superconducting element 20 from the relatively warm vessel 16, magnetic bearing 14, and fluid F.

Positioning of the superconducting element 20 in this vacuum chamber 25 is possible by virtue of the thermal link provided by the rod 22. The thermal isolation and separation provided by the chamber 25 allows for the superconducting element 20 to be placed in very close proximity to the outer wall 18 without affecting its temperature, or the temperature of the vessel 16. This allows the separation distance from the superconducting element 20 to the inner surface of the wall 18 to be narrowed significantly, such that in the preferred embodiment, the gap G between the two is under 10 millimeters, and can be as narrow as approximately 0.01 millimeters. This substantial reduction in the separation distance enhances the levitational stability, magnetic stiffness, and loading capacity of the bearing 14 without the concomitant cooling effects associated with prior art approaches for levitating magnetic bearings above cold superconducting elements.

In this first illustrated embodiment, the cooling source 24 is a separate, substantially contained cooling chamber 26 holding a cryogen C, such as liquid nitrogen. The chamber 26 is defined by an outer wall 28 that is substantially thermally separated from the outer wall 18 of the cryostat 12 to minimize heat transfer. An inlet I is provided through this wall 28 for introducing the cryogen into the cooling chamber 26. To permit any vapor P to escape from the chamber 26 as the cryogen C warms, an exhaust outlet O is also provided (see action arrows in FIG. 1 also designating the inlet and outlet). In the illustrated embodiment, the inlet I and outlet O lines may be formed of a material having a low thermal conductivity, such as an elongate, thin walled tube formed of non-magnetic stainless steel, and are sealed or welded in place to suspend the cooling chamber 26 in the cryostat 12. As should be appreciated by one of ordinary skill in the art, the use of a thin walled tube formed of a material having a low thermal conductivity, such as stainless steel, results in a negligible amount of thermal transfer from the inlet or outlet to the wall 18. The sealing or welding method employed should allow for the chamber 25 to be maintained in an evacuated state, if desired. Despite this illustration of one possible support arrangement, it should be appreciated that the use of any other support means that minimizes thermal transfer between the cooling chamber 26 and the cryostat wall or other housing 18 is also possible.

As should be appreciated from viewing FIG. 1, and as briefly noted in the foregoing description, the combination of the outer wall 18 and the inner cooling chamber 26 in this first embodiment defines the chamber 25 around the superconducting element 20. Preferably, this chamber 25 is evacuated to minimize heat transfer from the cooling chamber walls 28 and the superconducting element 20 to the outer wall 18 of the cryostat 12. The evacuation pressure is preferably at least $10^{-3}$ torr, and most preferably on the order of $10^{-5}$ torr, but of course may vary depending upon the requirements of a particular application. The important factor is that thermal transfer from the cooling source 24, which in this case is the cooling chamber 26 holding a cryogen C, and the superconducting element 20 to the outer wall 18 is minimized to avoid cooling the vessel 16 or fluid F held therein. Although a vacuum chamber 25 is proposed as one preferred manner of minimizing this thermal transfer, the use of other means to provide the desired thermal isolation is possible, such as by placing insulating materials or the like in the chamber 25.

As is known in the art, by cooling the superconducting element 20 in the presence of a magnetic field, it becomes capable of distributing the current induced by a permanent magnet such that the magnet levitates a certain distance above the superconducting element, depending primarily upon the intensity and the direction of the magnetic field generated by the levitating magnet. Although basically a repulsive force is created, the peculiar nature of the pinning forces generated actually tie the levitating magnet to the superconducting element as if the two were connected by an invisible spring. As should be appreciated, this form of attachment cannot be achieved in conventional levitation schemes for magnetic bearings that employ two opposed permanent magnets that merely repel each other, since no pinning forces act to tie the two magnets together, while at the same time provide a balancing repulsive force.

In the preferred embodiment of the present system 10, the element 20 providing the superconductive effects is a "high temperature" or "type II" superconductor. Most preferably, the superconducting element 20 is formed of a relatively thin cylindrical pellet of melt-textured Yttrium-Barium Copper Oxide that, upon being cooled to a temperature of approximately 77-78 Kelvin using a cooling source 24, such as the illustrated liquid nitrogen chamber 26, exhibits the desired levitational properties in a permanent magnet. Of course, the use of other known superconducting materials having higher or lower operating temperatures is also possible, and my prior U.S. Pat. No. 5,567,672 is incorporated herein by reference for, among other things, the other high-temperature superconducting materials referenced therein.

The magnetic bearing 14 in the preferred embodiment includes a first permanent magnet 32 for positioning in the vessel 16 adjacent to the superconducting element 20 such that it levitates in the fluid F. Although the polarity of this first magnet 32 is not critical to creating the desired levitation, the magnet 32 is preferably disk-shaped and polarized in the vertical direction. This ensures that a symmetrical magnetic field is created by the magnet 32 and stable levitation results above the superconducting element 20, while at the same time free rotation relative to the vertical axis is possible.

In a version of the magnetic bearing 14 particularly adapted for use in relatively deep fluid vessels, a support shaft 34 is connected to and extends vertically from the first permanent magnet 32. Along the shaft 34, at least one, and preferably two, impeller assemblies 36 are carried that serve to provide the desired pumping, or in the case of FIG. 1, mixing action when the magnetic bearing 14 is rotated. Rotation of the levitating magnetic bearing 14 in the vessel 16 is achieved by a magnetic coupling formed between a second permanent magnet 38 (shown in dashed line outline in FIG. 1, but see also FIG. 2) and a drive magnet 40 positioned externally of the vessel 16. The drive magnet 40 is rotated by a drive means, such as an electric motor 42 or the like, and the magnetic coupling formed with the second permanent magnet 38 serves to transmit the driving torque to the bearing 14 to provide the desired pumping or mixing action. The direction of rotation is indicated by the action arrows shown in FIGS. 1 and 2 as being in the counterclockwise direction, but it should be appreciated that this direction is easily reversed by simply reversing the direction in which the drive magnet 40 is rotated.

In operation, and in practicing one possible method of pumping or mixing a fluid disclosed herein, the vessel 16 containing the fluid F and magnetic bearing 14 are together placed external to the wall 18 of the cryostat 12 adjacent to the superconducting element 20, which is placed in the evacuated or insulated chamber 25. When the first disk-shaped permanent magnet 32 is brought into the proximity of the superconducting element 20, the symmetrical magnetic field generated causes the entire bearing 14 to levitate in a stable fashion above the bottom wall of the vessel 16. This levitation brings the second permanent magnet 38 into engagement with the drive magnet 40 to form the desired magnetic coupling. In addition to transmitting the driving torque, this magnetic coupling also serves to stabilize rotation of the magnetic bearing 14. The motor 42 or other motive device is then engaged to cause the drive magnet 40 to rotate, which in turn induces a steady, stable rotation in the bearing 14. Rotating impeller assemblies 36 then serve to mix or pump the fluid F in a gentle, yet thorough fashion.

Since the bearing 14 fully levitates and can be completely submerged in the fluid, the need for mixing or stirring rods penetrating through the vessel 16 in any fashion is eliminated. The concomitant need for dynamic shaft seals or support bearings in the vessel walls is also eliminated. A related advantage is that the vessel 16 containing the fluid F and the magnetic bearing 14 can be completely sealed from the outside environment before mixing to provide further assurances against leakage or contamination. Yet another related advantage discussed in detail below is that the vessel 16 and magnetic bearing 14 can be formed of relatively inexpensive, disposable materials and simply discarded once mixing is complete. As should be appreciated, this advantageously eliminates the need for cleanup and sterilization of the magnetic bearing 14 and vessel 16. Thus, by completely sealing a disposable vessel, such as a plastic container or flexible bag containing the magnetic bearing and fluid prior to mixing, the entire assembly can simply be discarded once the fluid contents are recovered. This reduces the risk of exposure both during and after mixing in the case of hazardous fluids, and also serves to protect the fluid from contamination prior to or during the pumping or mixing operation.

Figure 2:
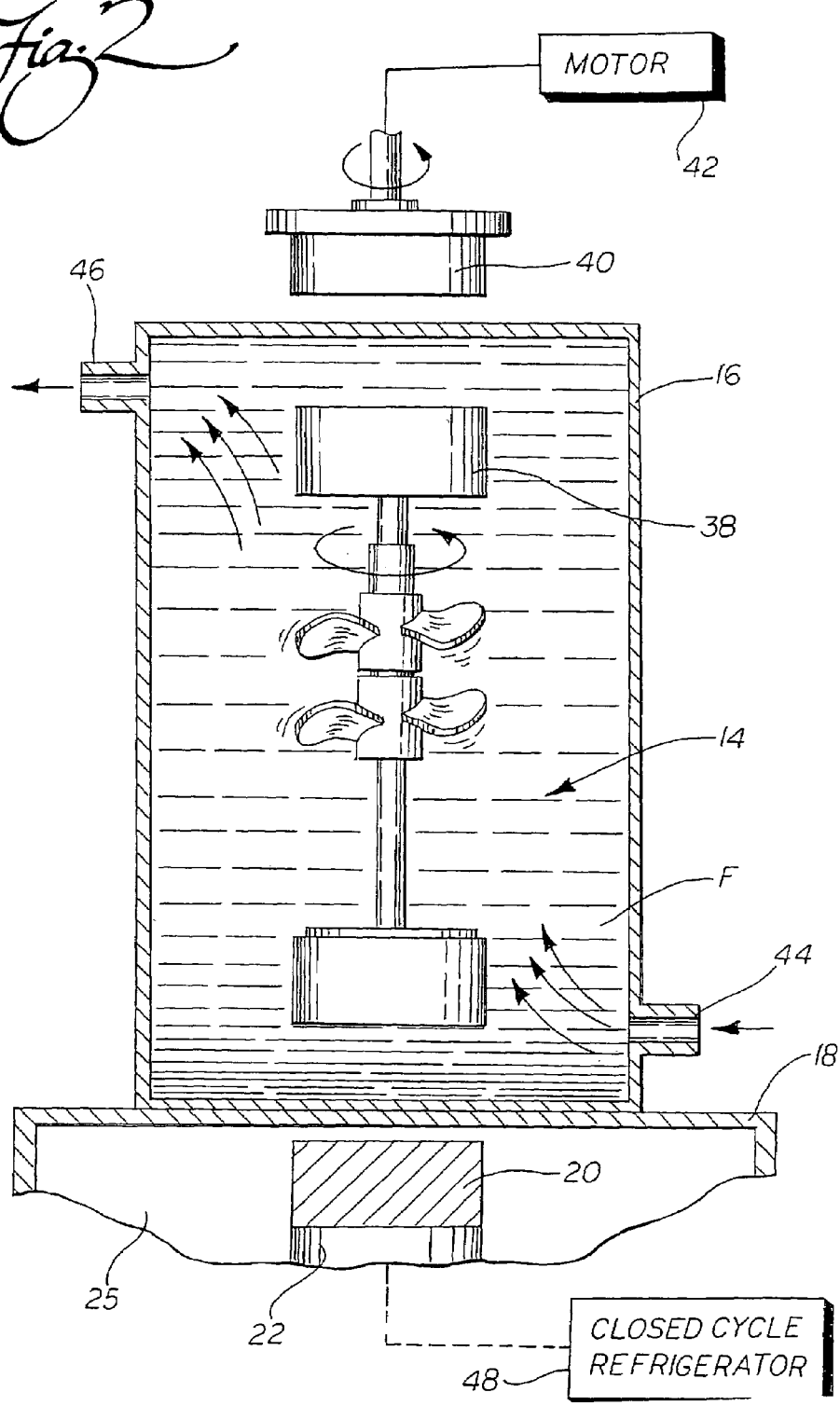
FIG. 2 is an enlarged cross-sectional, partially cutaway, partially schematic view of an embodiment wherein the rotating, levitating magnetic bearing is used to pump a fluid through a vessel positioned adjacent to the housing for the superconducting element and the cooling source is a closed cycle refrigerator.

An alternative version of this first possible embodiment of the system 10 of the present invention particularly adapted for pumping a fluid F is shown in FIG. 2. In this version, the vessel 16 includes at least one fluid inlet 44 and at least one outlet 46. The magnetic bearing 14 preferably carries rotating impeller assemblies 36 that serve to provide the desired pumping action by forcing fluid F from the inlet 44 to the outlet 46 (see action arrows). By increasing or decreasing the rotational speed of the motor 42 or other motive device, or adjusting the size, shape or style of the bearing 14, impeller blades 36, or substituting a different design altogether, a precise level of pumping action may be provided.

Another possible modification shown in FIG. 2 is to use a closed cycle refrigerator 48 to provide the necessary cooling for the superconducting element 20 instead of a cryostat with a liquid cryogen as the cooling source. The refrigerator 48 can be positioned externally to a housing 18 containing the superconducting element 20, which may be the equivalent of the cryostat outer wall 18 previously described. As with the first embodiment, a chamber 25 is defined by the housing 18. This chamber 25 is preferably evacuated or filled with other insulating materials to minimize thermal transfer from the superconducting element 20 to the housing 18. However, since no cooling source 24 is contained within the housing 18, it is not actually a "cryostat" as that term is commonly defined. Nevertheless, the desired dual levels of thermal separation are still possible, and the concomitant advantages provided, since: (1) the cooling source 24, 48 is positioned away from the housing 18 and, thus, the vessel 16, magnetic bearing 14, and fluid F; and (2) the housing 18 still separates and defines a chamber 25 that thermally isolates the superconducting element 20 and the vessel 16. In yet another alternate arrangement, the refrigerator 48 can be used as a primary cooling source, with the cryogenic chamber (not shown) serving as a secondary or "backup" cooling source in the event of a power outage or mechanical failure.

Figure 3:
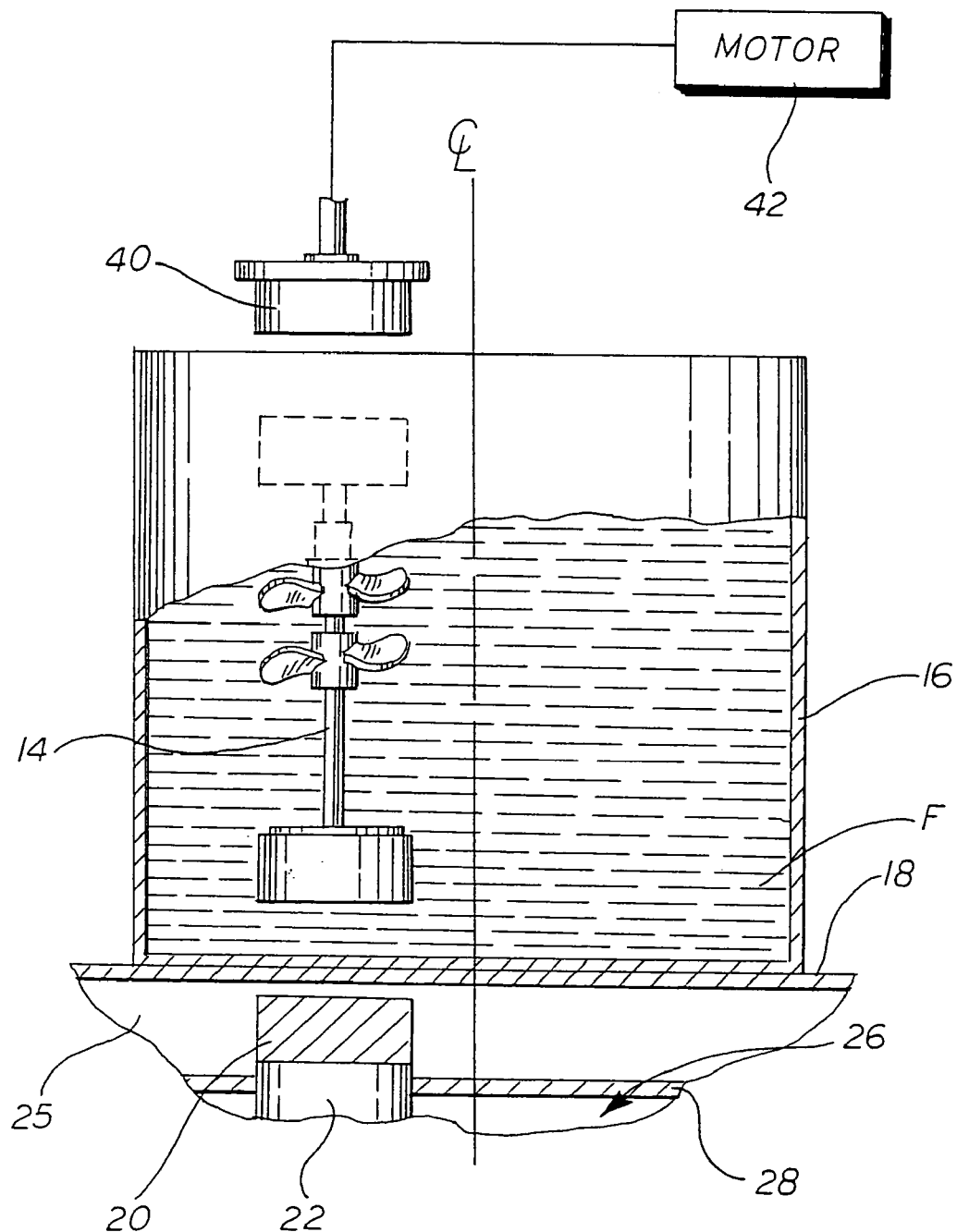
FIG. 3 is a partially cross-sectional, partially cutaway, partially schematic view of the system of the first embodiment wherein the superconducting element, vessel, magnetic bearing, and drive magnet are axially aligned, but moved off-center relative to the vertical center axis of the vessel.

In accordance with another of the many important aspects of the present system 10, the absence of a mixing rod or other mechanical stirrer extending through a wall of the vessel 16 also allows for placement of the magnetic bearing 14 at an off-axis position, as shown in FIG. 3. Specifically, the superconducting element 20, magnetic bearing 14, and drive magnet 40 are all axially aligned away from the vertical center axis of the vessel 16. One particular advantage of using this approach is that the magnetic bearing 14 may be rotated at a very low speed while the vessel 16 is also rotated about its center axis. This advantageously ensures that gentle, yet thorough mixing, is achieved, which is particularly advantageous for use with fluids that are sensitive to shear stress. As should be appreciated, this arrangement can be used both whether the vessel 16 is completely sealed, provided with an inlet 44 and an outlet 46 for pumping as shown in FIG. 2, or open to the ambient environment. For purposes of illustration only, FIG. 3 shows the cryostat 12 of the embodiment shown in FIG. 1 having an outer wall 18 and a cooling chamber 26 defined by a wall 28. However, it should be appreciated that use of the housing 18 and closed-cycle refrigerator 48 of the second embodiment of FIG. 2 as part of the "cryostat" is also possible with this arrangement.

Through experimentation, it has been discovered that when the magnetic bearing 14 of the type described for use in this first possible embodiment is employed, providing the requisite degree of stability to ensure that all contact with the side walls of the container 16 is avoided may in some instances be a concern. Thus, to ensure that the magnetic bearing 14 rotates with exceptional stability and such deleterious contact is completely avoided, the second permanent magnet 38 and the drive magnet 40 are each provided with at least two pairs, and preferably four pairs of cooperating sub-magnets 50a, 50b. As shown in FIGS. 4a and 4b, these magnets 50a, 50b have opposite polarities and thereby serve to attract each other and prevent the levitating magnetic bearing 14 from moving from side-to-side to any substantial degree. However, the attractive force is counterbalanced by the combined spring-like attractive and repulsive levitational/pinning forces created between the first permanent magnet 32 and the superconducting element 20 when cooled. This avoids the potential for contact with the upper wall of the vessel 16, if present. Overall, the magnetic bearing 14 is capable of exceptionally stable rotation using this arrangement, which further guards against the undesirable frictional heating or shear stress created if the rotating bearing 14, or more particularly, the first and second permanent magnets 32, 38 or the blades of the impeller assemblies 36 could move into close proximity with the bottom or side walls of the vessel 16.

Figure 4C:
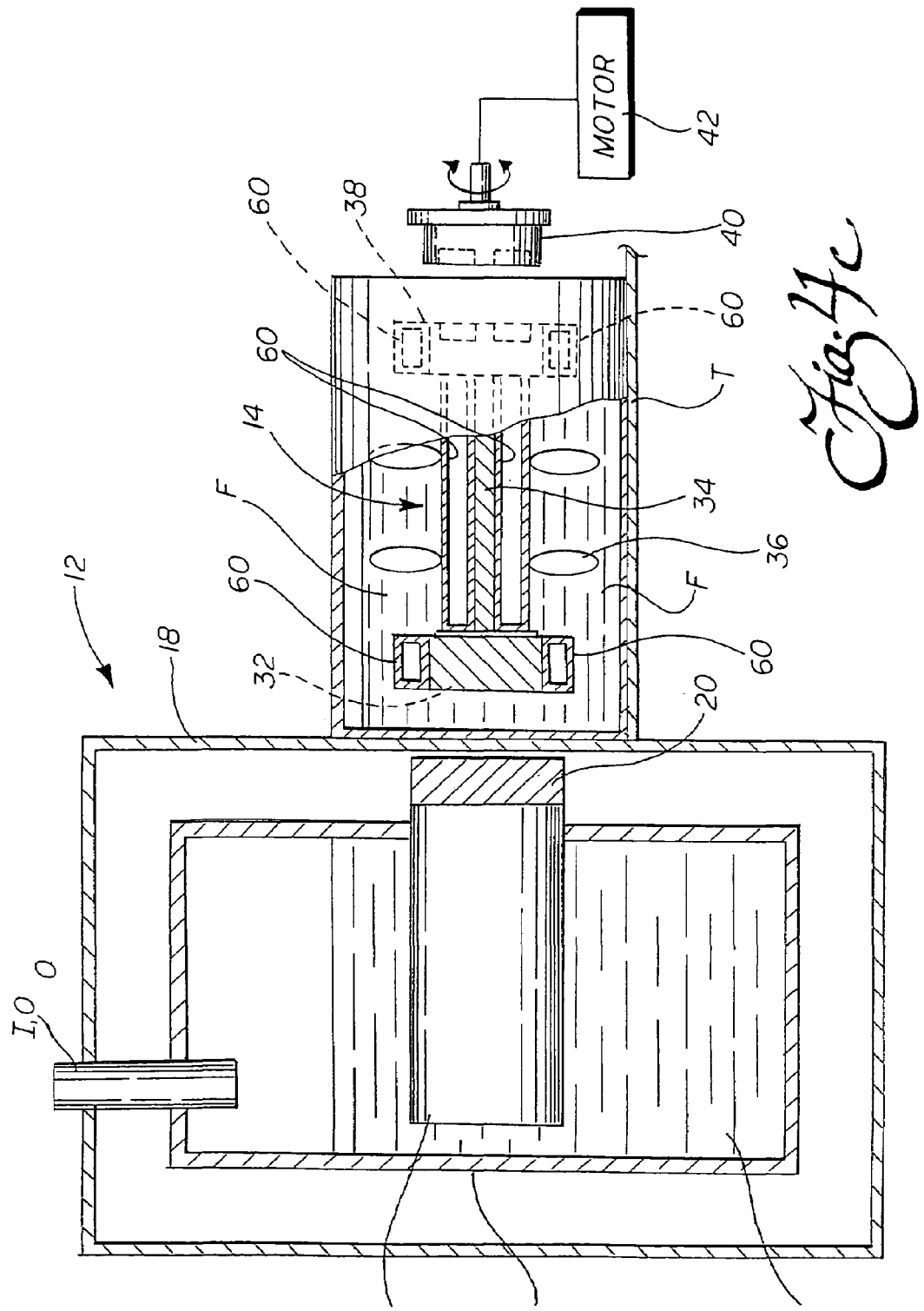
FIG. 4c is one possible embodiment of the pumping or mixing system including a bearing having a plurality of chambers for holding a substance that is lighter than the surrounding fluid, such as air, that assists in levitating the bearing.

As should be appreciated, it is possible to rearrange the components of the system 10 such that the levitation and driving forces are provided from other areas of the vessel, rather than from the top and bottom of the vessel. Thus, as shown in FIG. 4c, the cryostat 12 or other housing for containing the superconducting element 20 may be positioned adjacent to one side of the vessel 16, while the drive magnet 40 is positioned adjacent to the opposite side. In that case, the bearing 14 may be turned on its side and supported by a separate stable support structure, such as a table T or the like. The vessel 16 is shown as being sealed, but it should be appreciated that any of the vessels disclosed herein may be employed instead, including even a pipe.

To assist in levitating the bearing 14 in either the embodiment of FIGS. 1 or 2 or the other embodiments disclosed herein, at least one, and preferably a plurality of chambers 60 are provided for containing a substance that is lighter than the surrounding fluid F. The chambers 60 may be provided adjacent to each magnet 32, 38 in the bearing 14, as well as around the shaft 34, if desired. In the preferred embodiment where the fluid F is or has a specific gravity similar to that of water, the substance contained in the chambers 60 may be air. However, in more viscous fluids, such as those having a specific gravity more like glycerin, it may be possible to use lighter fluids, such as water, even lighter gases, or combinations thereof. These chambers 60 thus serve to assist in levitating the bearing 14 by helping it "float" in the fluid F. However, the "pinning" force created by the superconducting element 20, plus the levitating and aligning force created between the second permanent magnet 38 and the driving magnet 40, both also serve to assist in keeping the bearing 14 in the proper position as it rotates. In the case of disk or pancake shaped permanent first and second magnets 32, 38 and a cylindrical shaft 34, each chamber 60 is preferably annular. Instead of fluid-filled chambers, the use of other buoyant materials is also possible to provide the levitation-assist function.

As previously mentioned, one of the many advantages of the system 10 of the present invention is that, since the magnetic bearing 14 levitates in the fluid F and no mixing or stirring rods are required for rotation, the vessel 16 can be completely sealed from the outside ambient environment. Thus, by forming the bearing 14 and vessel 16 of relatively inexpensive or disposable materials, both can simply be discarded after mixing is completed and the fluid F is recovered. Of course, such disposable materials can also be used to form the vessel 16 designed for pumping fluids (FIG. 2), or to form the open-top container for mixing fluids to avoid the need for clean up or sterilization once the operation is complete.

It should also be appreciated that the magnetic bearing 14 illustrated is an example of one preferred arrangement only, and that other possible configurations are possible. For instance, impeller blades are not required, since a disk-shaped magnetic bearing itself will create some mixing action simply by rotating. If present, the blade or blades could simply be placed circumferentially around the disk-shaped first permanent magnet 32 to reduce the length of the shaft 34, or eliminate it altogether, especially if the vessel 16 has a relatively small vertical dimension. Instead of a bladed impeller assembly 36, the use of other structural arrangements is also possible, such as disk-shaped wheels having vanes or like structures designed to create more or less efficient rotation, and a concomitant increase in the desired mixing or pumping action when rotated. Depending on the depth of the vessel 16, the length of the shaft 34, if present, can also be increased or decreased as necessary. All components forming the magnetic bearing in any embodiment described above may be coated with TEFLON or other inert materials to reduce the chances of contamination or corrosion, as well as to facilitate clean up, if required.

Of course, besides use in the mixing or pumping of small batches of fluid solutions or suspensions used during experimentation and research in the laboratory setting, all components are also easily scaled up for use in industrial or commercial pumping or mixing operations, such as those commonly used in the manufacture of pharmaceuticals on a large-scale basis. The levitation of the magnetic bearing can still be readily achieved in systems of much greater capacity than the one shown for purposes of illustration in the drawings, thus making the present arrangement particularly well-suited for the commercial production of pharmaceuticals or any other solutions or suspensions that require gentle, yet thorough mixing during processing.

Experiments conducted to date have demonstrated the efficacy of the system 10 described above. The set-up utilized in conducting these experiments included a magnetic bearing having axially aligned upper and lower magnets and an impeller assembly mounted on a vertically extending support shaft, as shown in FIG. 1. A cylindrical pellet of melt-textured $YBa_2Cu_3O_{7+x}$ having a diameter of 30 millimeters and a thickness of 25 millimeters was used as the superconducting element and placed in a cryostat having a configuration similar to the one shown in FIG. 1. The cryostat included a cooling chamber filled with approximately 1 liter of liquid nitrogen. A Nd—Fe—B permanent magnet with a surface field intensity of 0.4 Tesla was used as the lower, first permanent magnet.

Experiments conducted using this set-up demonstrated that the desired exceptionally stable levitation of the magnetic bearing above the top surface of the cryostat in a vessel filled with a relatively warm fluid was possible. A separation distance of up to seven millimeters was achieved, and the levitation was stable for up to five hours using just a liter of liquid nitrogen as the cryogen. In the first experiment using this set up, water was selected as a model low viscosity fluid. Rotational speeds of up to 600 rpm were achieved—this upper limit being defined by only the limited capabilities of the motor used to rotate the drive magnet in this experiment. No decoupling or instability in the magnetic bearing was observed at any speed. In the case of glycerin, a model high viscosity fluid, a maximum rotational speed of 60 rpm was achieved before some decoupling of the magnetic bearing was observed. To further demonstrate the mixing capabilities using the proposed system, SEPHADEX powder (dry bead, 50-150 micron diameter) was placed on the bottom of a water-filled vessel and the levitating magnetic bearing rotated. A uniform suspension was achieved after approximately five minutes of mixing.

As should be appreciated, the system 10 described above and shown in FIGS. 1-4 is based on a stationary superconducting element 20 and a magnetic bearing 14 that, in addition to a "levitation" magnet, includes one or more separate driven magnets for coupling with a drive mechanism positioned at the opposite end of the vessel or container relative to the superconducting element. However, other embodiments of the pumping or mixing system may include a levitating, rotating bearing with magnets that are simultaneously used not only for levitation, but also for transmitting driving torque. In one embodiment, this driving torque is provided by the pinning forces that couple the magnetic bearing with a rotating superconducting element. Thus, the superconducting element causes the bearing to rotate, even though there is no physical contact between the two elements.

Figure 5:
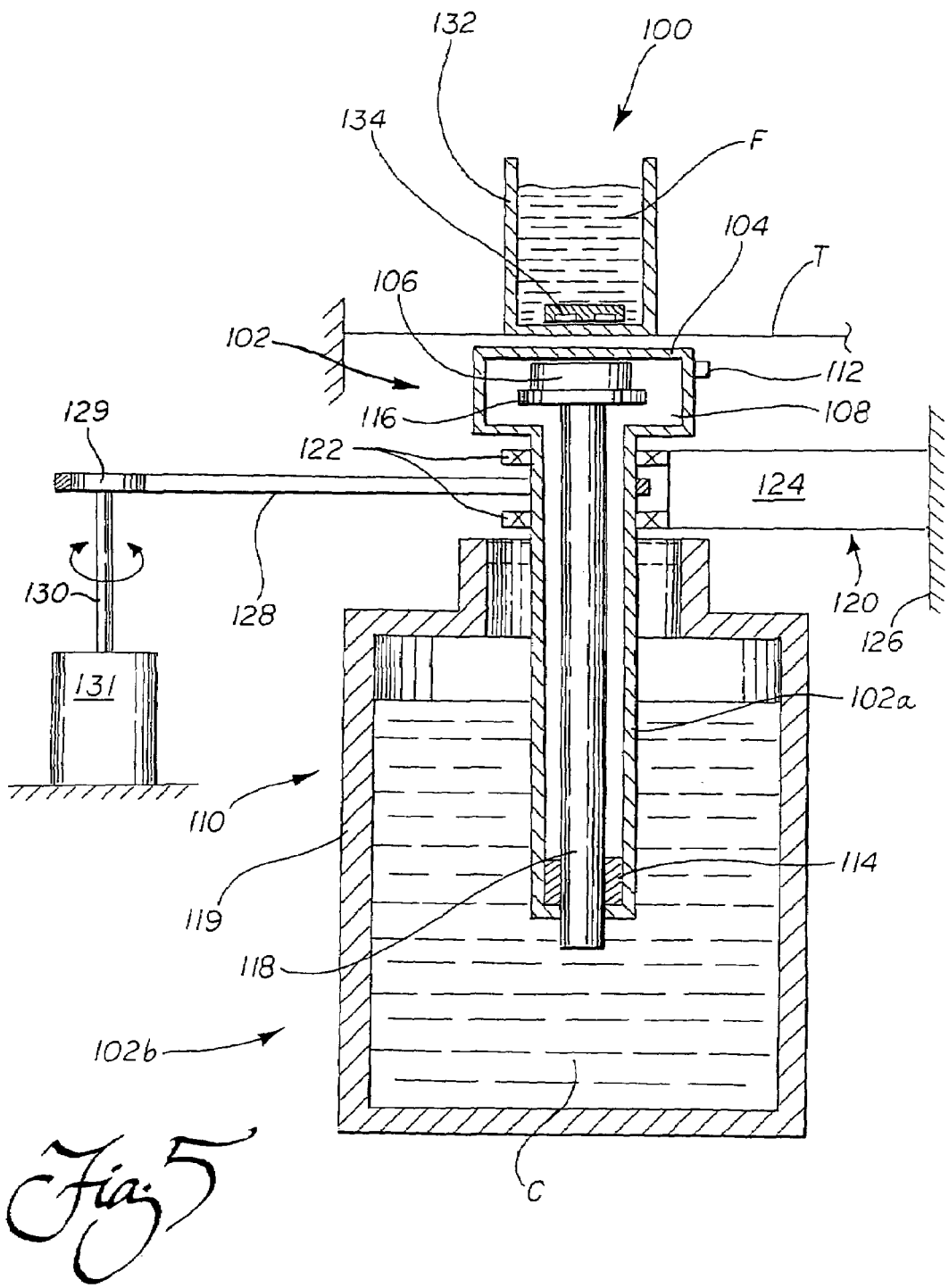
FIG. 5 is a partially cross-sectional, partially schematic side view of a second possible embodiment of a pumping or mixing system using a magnetic bearing levitated by a thermally isolated cold superconducting element wherein the motive force for rotating the bearing in the vessel is provided by rotating the superconducting element itself.

More specifically, and in accordance with this second possible embodiment of the present invention illustrated in FIG. 5, the pumping or mixing system 100 includes a cryostat 102, which may be formed of two separate components: a first component 102a including an outer wall 104 that surrounds a relatively thin, disk-shaped superconducting element 106 to define a chamber 108, and a second component 102b including the cooling source 110. Preferably, the outer wall 104 is formed of thin, non-magnetic material, such as non-magnetic stainless steel or the like, but the use of other materials is possible, as long as they do not interfere with the operation of the system 100 and have relatively poor thermal conductivity. The chamber 108 surrounding the superconducting element 106 may be evacuated or insulated as described above to thermally isolate and separate it from the wall 104. However, as noted further below, it is possible to eliminate the chamber 108 entirely in the case where a non-temperature sensitive fluid is being pumped or mixed.

In the case where the chamber 108 is evacuated, a valve 112 may be provided in the outer wall 104 for coupling to a vacuum source, and an optional getter 114 (such as an activated carbon insert or the like) may be positioned in the chamber 108 for absorbing any residual gases and ensuring that the desired evacuation pressure is maintained. As with the embodiments described above, the evacuation pressure is preferably on the order of $10^{-3}$ torr or greater.

The superconducting element 106 is supported in the chamber 108 independent of the outer wall 104 of the first portion 102a of the cryostat 102. The support may be provided by a platform 116 that is in turn enclosed by wall 104 and supported at one end of an elongated thermal link 118, preferably formed of metal or another material having a high degree of thermal conductivity (e.g., 50 Watts/Kelvin or higher). To supply the necessary cooling to the superconducting element, the opposite end of the elongated thermal link 118 is positioned in contact with the cooling source 110, which as described above forms a part of the second component 102b of the "cryostat" 102 (the term cryostat being used throughout to denote a structure or combination of structures that are capable of holding and maintaining a superconducting element in a cold state, whether forming a single unit or not). The cooling source 110 is illustrated as an open-top container 119, such as a Dewar flask, containing a liquid cryogen C, such as nitrogen. However, it is also possible to use a closed-cycle refrigerator or any other device capable of supplying the cooling necessary to levitate a magnet above a superconducting element after field cooling is complete. In the case where the wall 104 of the first portion 102a of the cryostat 102 makes contact with the cryogenic fluid C, as illustrated, it should be appreciated that there is only negligible thermal transfer to the portion of the wall 104 adjacent the vessel 132, since: (1) the wall 104 may be formed of a thin material having low thermal conductivity; and (2) the portion of the wall 104 adjacent to the vessel is surrounded by the ambient, room-temperature environment.

To permit the superconducting element 106 to rotate, a roller bearing assembly 120 comprising one or more annular roller bearings 122 supports the first portion of the cryostat 102a, including the wall 104 defining the chamber 108. As should be appreciated from viewing FIG. 5, these roller bearings 122 permit the first portion of the cryostat 102a housing the superconducting element 106 to rotate about an axis, which is defined as the axis of rotation. A bearing housing 124 or the like structure for supporting the bearing(s) 122 is secured to an adjacent stable support structure 126. In the illustrated embodiment, a motive device includes an endless belt 128 that serves to transmit rotational motion from the pulley 129 keyed or attached to the shaft 130 of a motor 131 to the first portion of the cryostat 102a. The motor 131 may be a variable speed, reversible electric motor, but the use of other types of motors to create the rotary motion necessary to cause the superconducting element 106, and more particularly, the first portion of the cryostat 102a housing the superconducting element 106, to rotate is possible.

The vessel 132 containing the fluid to be mixed (which as described below can also be in the form of a centrifugal pumping head for transmitting a fluid) is positioned adjacent to the rotating superconducting element 106, preferably on a stable support surface T fabricated of a material that does not interfere with the magnetic field created by the bearing 134. As previously noted, the vessel 132 can be a rigid vessel of any shape (open top, sealed having an inlet or outlet, cylindrical with a hollow center, such as a pipe, or even a flexible plastic bag (by itself, with rigid inserts, or inserted into a rigid or semi-rigid vessel)). The only requirement is that the vessel 132 employed is capable of at least temporarily holding the fluid F (or gas) being mixed or pumped.

To create the desired mixing action in this embodiment, a magnetic bearing 134 is positioned in the vessel 132 and simultaneously levitated and rotated by the superconducting element 106. More specifically, the first portion of the cryostat 102a containing the superconducting element 106, thermal link 118, and the evacuated chamber 108 is rotated as a result of the rotational motion transmitted by the endless belt 128. This rotation causes the magnetic bearing 134 in the vessel 124 to rotate and either pump or mix the fluid F held therein. In the case where the chamber 104 is evacuated or insulated, the bearing 134 is rotated in a stable, reliable fashion while the desired thermal separation between the cold superconducting element 106 supplying the levitation force, the vessel 124, and hence the fluid F, is achieved. The magnetic bearing 134 may include a plurality of mixing blades B (see FIGS. 6a and 6b), vanes V (not shown, but see FIG. 7), or like structures to create an impeller. However, again referring back to FIG. 5, a low-profile, disk-shaped magnetic bearing 134 may also be used to provide the desired mixing action, especially for particularly delicate fluids, such as blood or other types of cell suspensions.

Figure 6A:
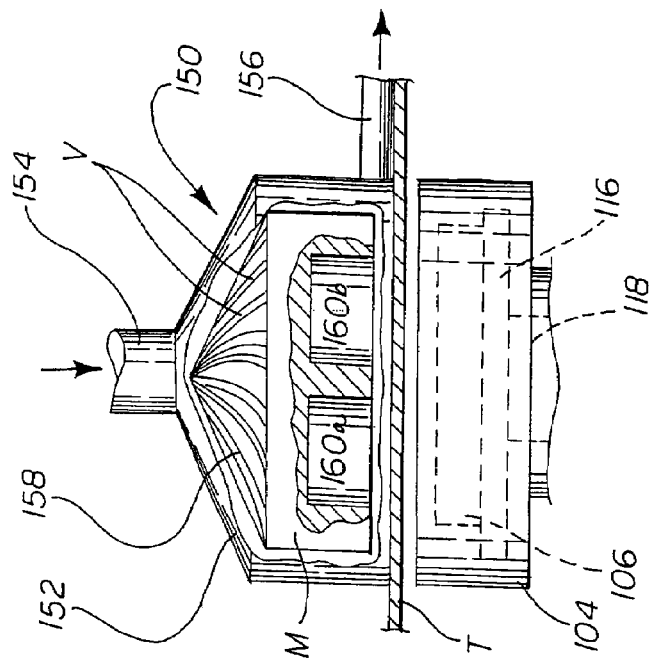
FIG. 6a is a top schematic view of one possible arrangement of the levitating magnetic bearing that may be driven by a rotating superconducting element.
Figure 6B:
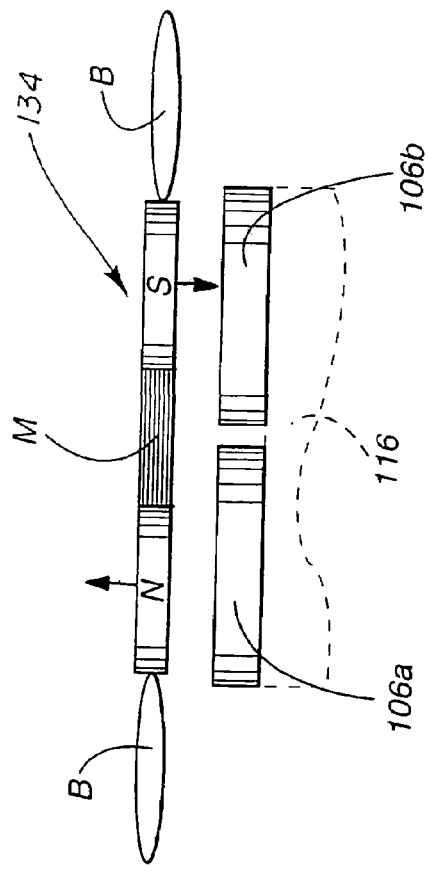
FIG. 6b shows the bearing of FIG. 6a levitating above a rotating superconducting element formed of two component parts.

As perhaps best understood by viewing FIGS. 6a and 6b together, the magnetic bearing 134 includes at least two magnets 135a, 135b. These magnets 135a, 135b not only serve to generate the magnetic field that causes the bearing 134 to levitate above the superconducting element 106, but also transmit rotational motion to the bearing. As should be appreciated by one of ordinary skill in the art, the magnetic field generated by the magnets 135a, 135b must be axially non-symmetrical relative to the axis of rotation of the superconducting element 106 in order to create the magnetic coupling necessary to efficiently transmit the rotary motion. In one embodiment, the magnets 135a, 135b are disk-shaped and polarized along a center vertical axis (see FIG. 6b, showing permanent magnets 135a, 135b of alternating polarities (S-South; N-North) levitating above a pair of superconducting elements 106a, 106b, with the corresponding action arrows denoting the direction and axis of polarity). These magnets 135a, 135b can be fabricated from a variety of known materials exhibiting permanent magnetic properties, including, but not limited to, Neodymium-Iron-Boron (NdFeB), Samarium Cobalt (SmCo), the composition of aluminum, nickel, and cobalt (Alnico), ceramics, or combinations thereof. The magnets 135a, 135b may be connected by a piece of a matrix material M, such as plastic. Alternatively, the magnets 135a, 135b may each be embedded in separate pieces of a matrix material M, or may be embedded in a single unitary piece of material (not shown). Also, as previously mentioned, the bearing 134 may carry one or more optional blades B, vanes or like structures to enhance the degree of pumping or mixing action supplied by the bearing upon being rotated.

In another possible embodiment, the second portion of the cryostat 102b including the cooling source (either a liquid cryogen container (open top, sealed with inlet/outlet ports, or a refrigerator)) may be rigidly attached to the first portion 102a and both components may be simultaneously rotated together (see the dashed lines at the top of the open cooling container 119 in FIG. 5). The rotational motion may be supplied by an endless belt/motor combination, as described above, or alternatively may be provided through a direct coupling between the second portion of the cryostat 102b (comprising any type of cooling source) and an inline shaft of a motor or similar motive device (not shown).

As briefly mentioned above, it is possible to use this embodiment of the system 100 without evacuating, insulating, or otherwise thermally separating the superconducting element 106 from the ambient environment, such as for mixing or pumping cold (cryogenic) or non-temperature sensitive fluids. In that case, there is no specific need for a wall 104 or chamber 108 surrounding the superconducting element 106, since there is no need to thermally separating it from the structure supporting the vessel 132. Even with this modification, reliable and stable levitation of the bearing 134 is still achieved.

Figure 7:
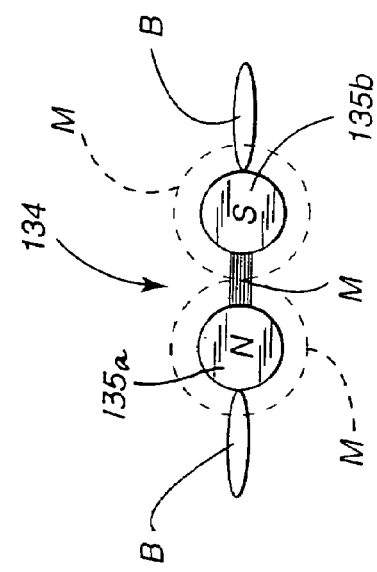
FIG. 7 is a partially cutaway, partially cross-sectional schematic side view of a vessel in the form of a centrifugal pumping head, including a levitating, rotating magnetic bearing for pumping fluid from the inlet to the outlet of the centrifugal pumping head.

From the foregoing, it should be appreciated that the same driving mechanism and cryostat shown in FIG. 5 can be used for pumping a fluid instead of mixing it. One version of a vessel 132 in the form of a centrifugal pumping head 150 is shown in FIG. 7. This pumping head 150 includes a pumping chamber 152 having an inlet 154 and an outlet 156 (which of course, could be reversed, such as in a non-centrifugal pumping head (see FIG. 2)). The chamber 150 contains the levitating magnetic bearing 158, which as shown may include a plurality of vanes V, or may alternatively carry a plurality of blades (not shown). At least two permanent magnets 160a, 160b having different polarities are embedded or otherwise included in the bearing 158, which may be substantially comprised of an inert matrix material M having any particularly desired shape to facilitate the pumping or mixing action. As described above, these magnets 160a, 160b provide both levitation and torque transmission as a result of the adjacent rotating superconducting element 106.

As should be appreciated, one advantage of providing the driving force for the levitating bearing 158 from the same side of the vessel/pumping head 150 from which the levitating force originates is that the fluid inlet 154 (or outlet 156, in the case where the two are reversed) may be placed at any location along the opposite side of the vessel/pumping head 150, including even the center, without interfering with the pumping or mixing operation. Also, this same side of the vessel/pumping head 150 may be frusto-conical or otherwise project outwardly, as illustrated, without interfering with the driving operation or necessitating a change in the design of the magnetic bearing 158.

Figures 8A, 8B:
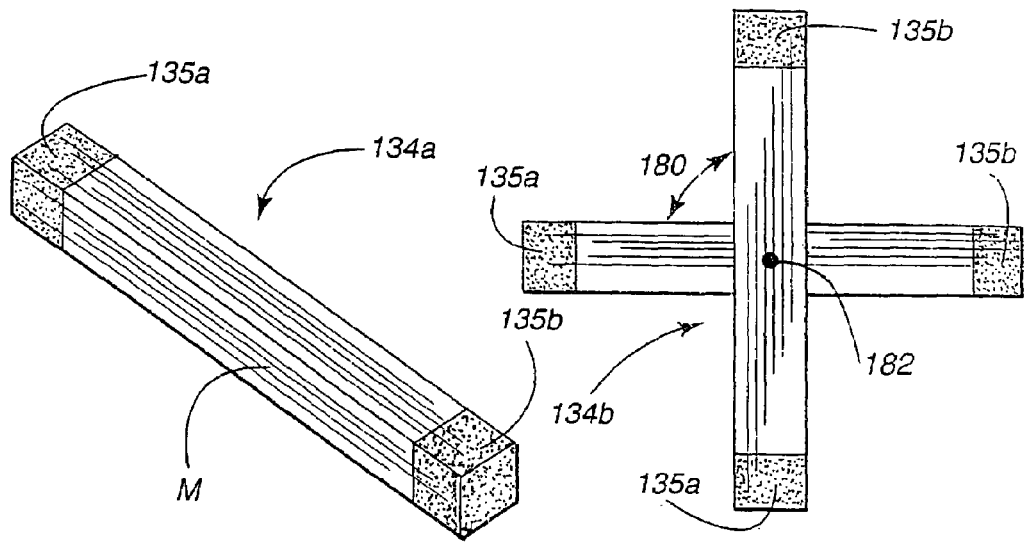
FIG. 8a shows an alternate embodiment of a magnetic bearing especially adapted for use in a vessel or container having a relatively narrow opening.
FIG. 8b shows another alternate embodiment of a magnetic bearing adapted especially for use in a vessel or container having a relatively narrow opening.

As briefly noted above, in some instances the opening in a vessel may be too small to permit an even moderately sized bearing 134 to be inserted into the fluid F. In such a case, alternate versions of a bearing 134 meeting this particular need are shown in FIGS. 8a-8c. In the first alternate version, the bearing 134a is in the form of a slender rod formed of an inert matrix material M carrying one of the levitating/driven magnets 135a, 135b at or near each end. As should be appreciated, this bearing 134a may be easily turned to an upstanding position and inserted in the opening. Upon then coming into engagement with the rotating superconducting element 106, the bearing 134a would simultaneously levitate and rotate to pump or mix a fluid held in the vessel. To further facilitate insertion in the narrow opening, the matrix material M may be an elastomeric material or another material having the ability to freely flex or bend.

A second version of a bearing 134b for use with a vessel having a narrow opening is shown in FIG. 8b. The bearing 134b includes first and second thin rods 180 formed of a matrix material M. The rods 180 each carry the levitating/driven magnets 135a, 135b at each end thereof, with at least two magnets having the identical polarity being held on each different rod. In one version, the rods 180 are pinned about their centers (note connecting pin 182) and are thus capable of folding in a scissor-like fashion. As should be appreciated from FIG. 8c, this allows the bearing 134b to be folded to a low-profile position for passing through the opening of the vessel 132. The rods 180 of the bearing 134b may then separate upon coming into engagement with the rotating superconducting element 106 positioned adjacent to the bottom of the vessel 132. Since magnets 135a or 135b having the same polarity are positioned adjacent to each other, the corresponding ends of the rods 180 repel each other as the bearing 134b rotates. This prevents the rods 180 from assuming an aligned position once in the vessel 132. As should be appreciated, instead of pinning two separate rods 180 together to form the bearing 134b, it is also possible to integrally mold the rods 180 of a flexible material to form a cross. This would permit the rods 180 of the bearing 134b to flex for passing through any narrow opening, but then snap-back to the desired configuration for levitating above the superconducting element 106.

In accordance with yet another aspect of the present invention, a third version of a pumping or mixing system 200 is disclosed. In this third embodiment, which is illustrated in FIGS. 9, 9a, 9b, and 10, the forces for driving and levitating the magnetic bearing 204 are supplied from the same side of a fluid vessel 202 (which is shown as an open-top container, but as described above, could be a sealed container, a pumping chamber or head, a flexible bag, a pipe, or the like). In this system 200, the magnetic bearing 204 actually includes two magnetic subsystems: a first one that serves to levitate the magnetic bearing 204, which includes a first magnet 206, preferably in the form of a ring, and a second magnetic subsystem that includes at least two alternating polarity driven magnets 208a, 208b, preferably positioned inside of the first, ring-shaped magnet 206, to transmit driving torque to the bearing (see FIGS. 9a and 9b).

Figure 9B:
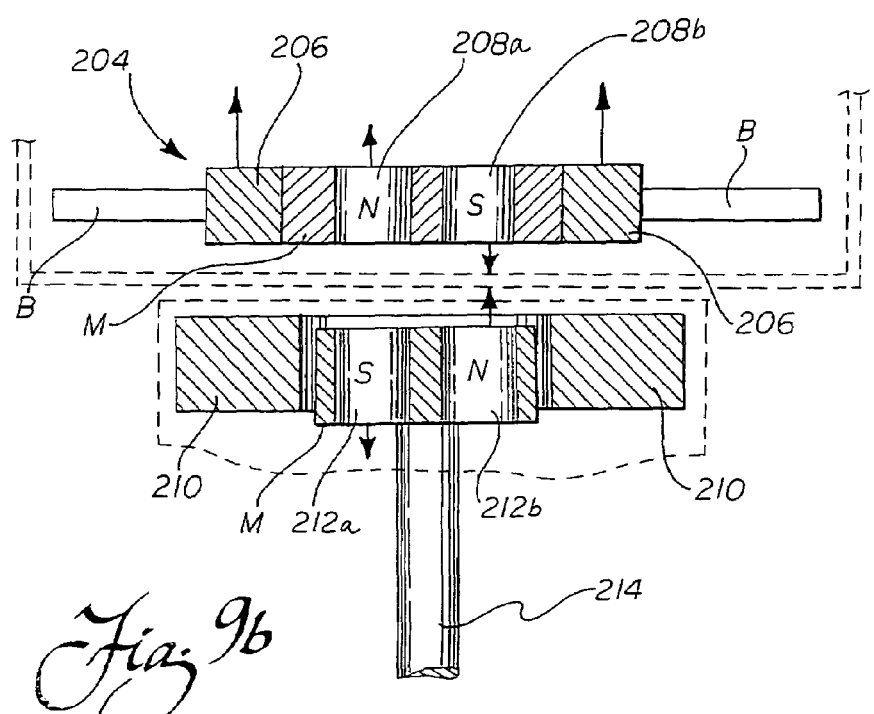
FIG. 9b is a partially cross-sectional side view of the magnetic bearing of FIGS. 9 and 9a levitating above the superconducting element, and illustrating the manner in which the driven magnets are coupled to the corresponding driving magnets to create the desired rotational motion.
Figure 9:
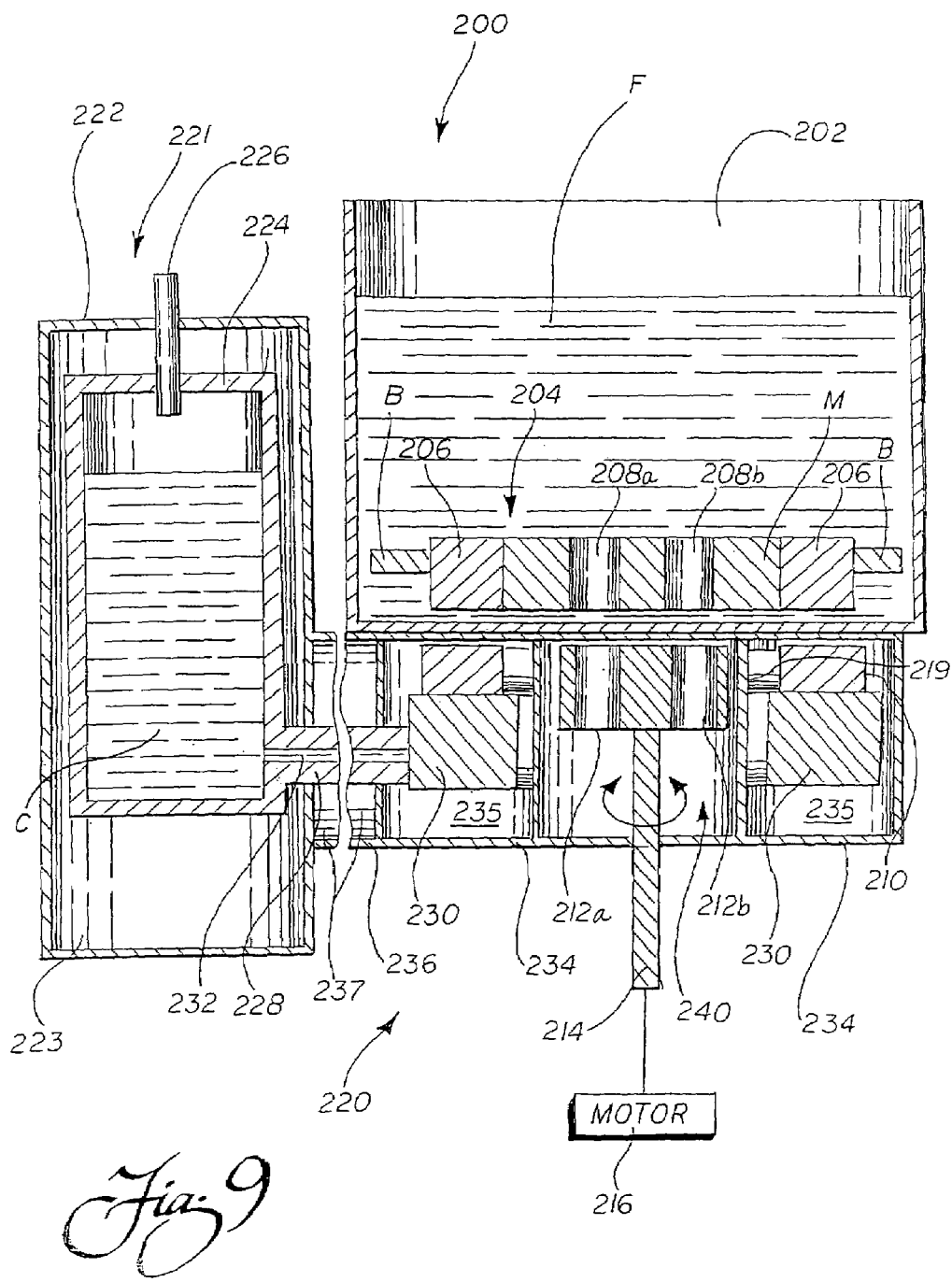
FIG. 9 is a partially cross-sectional, partially schematic side view of a second embodiment of a pumping or mixing system wherein separate levitating and driven magnets are carried on the same, low-profile magnetic bearing, with the levitation being supplied by a thermally isolated superconducting element and the rotary motion being supplied by a motive device including driving magnets coupled to a rotating shaft and positioned in an opening in the evacuated or insulated chamber for housing the superconducting element.

FIG. 9 shows one embodiment of the overall system 200 in which the ring-shaped permanent magnet 206 provides the levitation for the magnetic bearing 204. Polarization of the ring magnet 206 is vertical (as shown by the long vertical arrows in FIG. 9b). The driven magnets 208a, 208b are shown being disk-shaped and having opposite or alternating polarities (see corresponding short action arrows in FIG. 9b representing the opposite polarities) to form a magnetic coupling and transmit the torque to the levitating magnetic bearing 204. Levitation magnet 206 and driven magnets 208a, 208b are preferably integrated in one rigid structure such as by embedding or attaching all three to a lightweight, inert matrix material M, such as plastic or the like.

To correspond to the ring-shaped levitation magnet, the superconducting element 210 for use in this embodiment is annular, as well. This element 210 can be fabricated of a single unitary piece of a high-temperature superconducting material (YBCO or the like), or may be comprised of a plurality of component parts or segments. Upon being cooled to the transition temperature in the presence of a magnetic field and aligning with the ring-shaped permanent magnet 206 producing the same magnetic field, the superconducting ring 210 thus provides the combined repulsive/attractive, spring-like pinning force that levitates the magnetic bearing 204 in the vessel 202 in an exceptionally stable and reliable fashion. In FIG. 9, the vessel is shown as being supported on the outer surface of a special cryostat 220 designed for use with this system 200, a detailed explanation of which is provided in the description that follows. However, it is within the broadest aspects of the invention to simply support the vessel 202 on any stable support structure, such as a table (not shown), as long as it remains sufficiently close to the superconducting element 210 to induce the desired levitation in the magnetic bearing 204 held therein.

As in the embodiments described above, a motive device is used to impart rotary motion to the bearing 204, and is preferably positioned adjacent to and concentric with the annular superconducting element 210. One example of a motive device for use in the system 200 of this third embodiment includes driving magnets 212a, 212b that correspond to the driven magnets 208a, 208b on the bearing 204 and have opposite polarities to create a magnetic coupling (see FIG. 9). The driving magnets 212a, 212b are preferably coupled to a shaft 214 also forming part of the motive device. The driving magnets 212a, 212b may be attached directly to the shaft 214, or as illustrated in FIG. 9, may be embedded or attached to a matrix material (not numbered in FIG. 9, but see FIG. 9b). By positioning the driving magnets 212a, 212b close to the bearing 204, such as by inserting them in the opening or bore 219 defined by the annular superconducting element 210, and rotating the shaft 214 using a motor 216 also forming a part of the motive device, synchronous rotation of the levitating magnetic bearing 204 is induced. The magnetic bearing 204 may include one or more blades B that are rigidly attached to the ring or levitation magnet 206 (or any matrix material forming the periphery of the bearing 204). However, it remains within the broadest aspects of the invention to simply use a smooth, low-profile bearing (see FIG. 5) to provide the desired mixing action.

Figure 10:
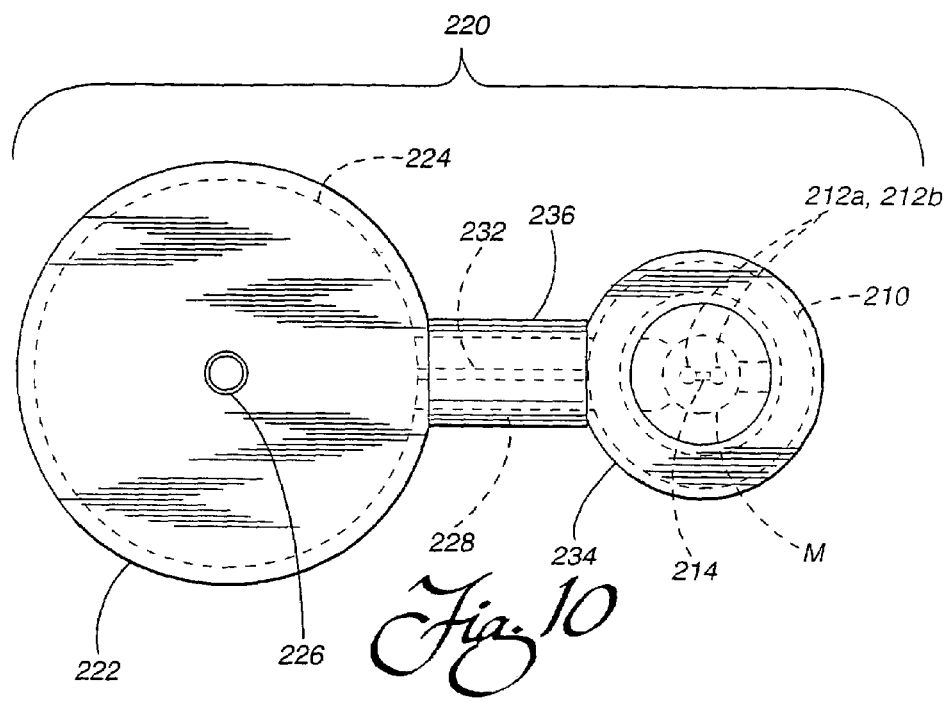
FIG. 10 is a top view of a most preferred version of a cryostat for use with the pumping and mixing system of the embodiment of FIG. 9.

As shown in FIGS. 9 and 10 and briefly mentioned above, the mixing or pumping system 200 including the bearing 204 comprised of the magnetic levitation ring 206 and separate driven magnets 208a, 208b may use a special cryostat 220 to ensure that reliable and stable rotation/levitation is achieved. As perhaps best shown in the cross-sectional side view of FIG. 9, the cryostat 220 includes a separate cooling source 221 for indirectly supplying the necessary cooling to the superconducting element 210, which as described below is supported and contained in a separate portion of the special cryostat 220. In the illustrated embodiment, the cooling source 221 (not necessarily shown to scale in FIG. 9) includes a container 222, such as a double-walled Dewar flask, in which a first chamber 224 containing a liquid cryogen C (nitrogen) is suspended. A second chamber 223 defined around the first chamber 224 by the double wall container 222 is preferably evacuated or insulated to minimize thermal transfer to the ambient environment, which is normally at room temperature. A port 226 is also provided for filling the suspended chamber 222 with the chosen liquid cryogen C, as well as for possibly allowing any exhaust gases to escape. As with the first and second embodiments described above, the cooling source 221 may instead take the form of a closed-cycle refrigerator (not shown), in which case the double wall container 222 may be entirely eliminated from the system 200.

A thermal link 228 between the cooling source (in the illustrated embodiment, the container 222) and a platform 230 suspended in the cryostat 220 support the superconducting ring 210. The use of the platform 230 ensures that the temperature of the superconducting element 210 is kept below the transition temperature, which in the case of a "high temperature" superconducting material (such as YBCO) most preferably ranges between 87-93 Kelvin. However, the use of the platform 230 is not critical to the invention or required as part of the special cryostat 220, since the thermal link 228 could extend directly to the superconducting element 210. The thermal link 228 may be a solid rod of material, including copper, brass, aluminum or any other material having a relatively high thermal conductivity.

Instead of a solid rod, it is also possible to provide an open channel 232 in the thermal link 228, especially when a liquid cryogen C capable of flowing freely, such as nitrogen, is used as the cooling source 221. This channel 232 allows the cryogen C from the suspended container 224 to reach the platform 230 directly. Of course, the direct contact with the cryogen C may provide more efficient and effective cooling for the superconducting element 210.

The ring-shaped platform 230 that supports the superconducting element(s) 210 and supplies the desired cooling via thermal conduction may be made of copper, brass, aluminum, or another material having good thermal conductivity. It may be in the form of a solid ring, as illustrated, or may be in the form of a hollow ring (such as a substantially circular or elliptical torus, not shown). This would allow the liquid cryogen C to flow completely around the ring to further increase the efficiency with which the cooling is transferred to the superconducting element 210. In any case, where a platform 230 is used, care should be taken to ensure full contact with at least a majority of the corresponding surface of the superconducting element 210 to ensure that the desired smooth, even, and reliable levitation results.

To reduce the thermal transfer to the vessel 202 in the case of pumping or mixing a temperature sensitive fluid, a ring-shaped wall or enclosure 234 surrounding the platform 230 and the annular superconducting element 210 defines a first chamber 235. In addition, a hollow cylindrical wall or enclosure 236 may also surround the thermal link 232 and define a second chamber 237. Preferably, these first and second chambers 235, 237 are evacuated or insulated to minimize thermal transfer between the ambient environment and the cold elements held therein. In a preferred embodiment, each enclosure 234, 236 is fabricated from non-magnetic stainless steel, but the use of other materials is of course possible, as long as no interference is created with the levitation of the magnetic bearing 204. As with the second embodiment described above, it is also possible to use the system 200 of the third embodiment to pump or mix cryogenic or non-temperature sensitive fluids, in which case there is no need to evacuate or insulate the enclosures 234, 236, or to even use the special cryostat 220 described herein.

As should be appreciated, it is possible to create the chambers 235, 237 defined by the enclosures 234, 236 and the chamber 223 such that all three are in fluid communication and thus represent one integrated vacuum space (not shown). This facilitates set-up, since all three chambers 223,235, 237 maybe evacuated in a single operation, such as by using a vacuum source coupled to a single valve (not shown) provided in one of the chambers. However, separately evacuating each chamber 223, 235, 237 is of course entirely possible. Also, instead of evacuating the chambers 223, 235, 237, some or all may be instead filled with an insulating material (not shown).

As should be appreciated, to rotate the magnetic bearing 204 in this embodiment, it is desirable to place the drive magnets 212a, 212b in close proximity to the bearing, but preferably on the same side of the vessel 202 as the superconducting element 210. Accordingly, the special cryostat 220, and more specifically, the wall or enclosure 234 defines a room-temperature cylindrical bore or opening 240 that allows for the introduction of the end of the shaft 214 carrying the driving magnets 212a, 212b, which are at room temperature. As a result of this arrangement, the shaft 214, which is part of the motive device, is concentric with the superconducting element 210. The shaft 214 is also positioned such that the driving magnets 212a, 212b align with the driven magnets 208a, 208b on the bearing 204 when the levitating magnet 206 is aligned with the superconducting element 210. Thus, despite being positioned adjacent to and concentric with the superconducting element 210, the shaft 214 and driving magnets 212a, 212b remain at room temperature, as does the vessel 202, the fluid F, and the magnetic bearing 204.

Figure 11:
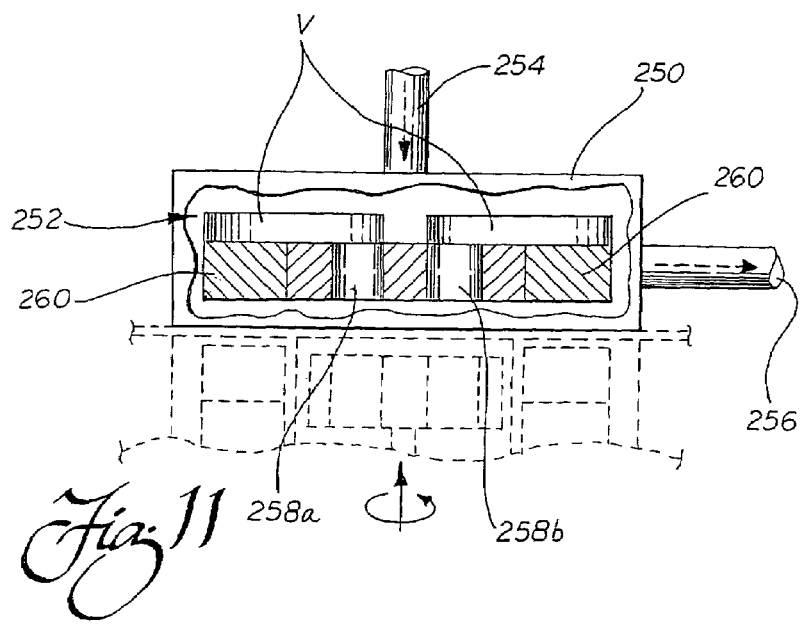
FIG. 11 is a partially cutaway, partially cross-sectional side schematic view of a centrifugal pumping head for use with the system of FIG. 9.

An example of one possible embodiment of a centrifugal pumping head 250 for use with the system 200 of FIG. 9 is shown in FIG. 11. The head 250 includes a levitating bearing 252 that carries one or more optional blades or vanes V (which are upstanding in the side view of FIG. 11), a fluid inlet 254 (which as should be appreciated can be in the center at one side of the pumping head 250 in view of the fact that the levitation and driving forces are both supplied from the same side of the vessel 202), a fluid outlet 256, driven magnets 258a, 258b, and a ring shaped levitation magnet 260.

Figure 12:
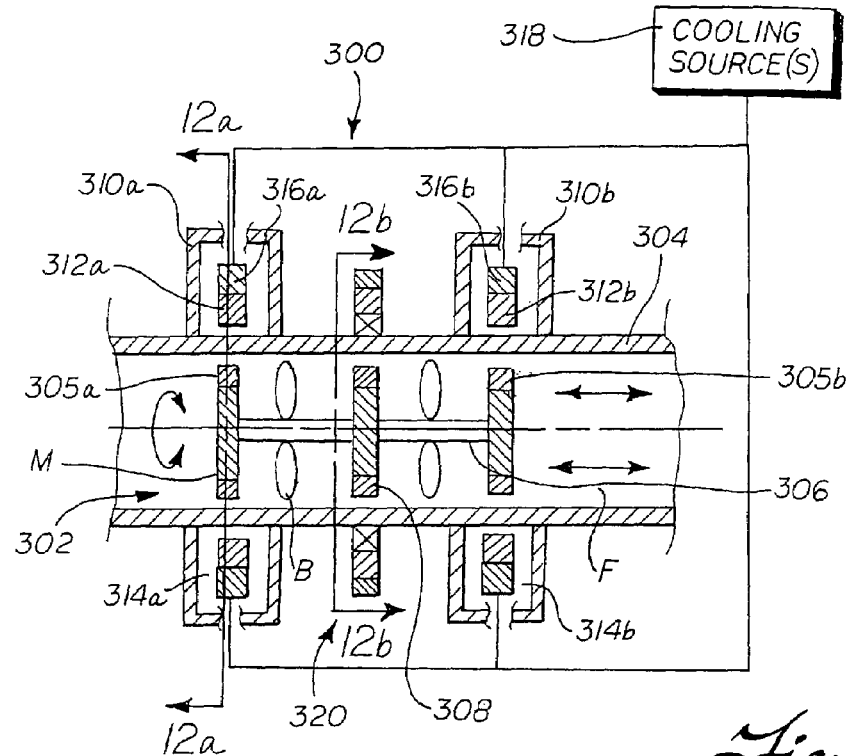
FIG. 12 is a cross-sectional side view of another possible embodiment of a pumping or mixing system of the present invention.

In yet another possible embodiment of the invention, as shown in the cross-sectional view of FIG. 12, the system 300 includes a magnetic bearing 302 adapted for inline use, such as when the vessel is in the form of a hollow pipe 304. The bearing 302 includes first and second spaced levitating magnets 305a, 305b, one of which is preferably positioned at each end to ensure that stable levitation is achieved. The magnets 305a, 305b preferably correspond in shape to the vessel, which in the case of a pipe 304, means that the magnets are annular. The magnets 305a, 305b are carried on a shaft 306 forming a part of the bearing 302, which further includes a driven magnet 308. The driven magnet 308 may be comprised of a plurality of sub-magnets 308a . . . 308n having different polarities and arranged in an annular configuration to correspond to the shape of the pipe 304 serving as the vessel in this embodiment (see FIG. 12b). All three magnets 305a, 305b, and 308 may be embedded or attached to an inert matrix material M, such as plastic, that provides the connection with the shaft 306. The shaft 306 of the bearing 302 may also carry one or more blades B.

First and second cryostats 310a, 310b are also provided. As perhaps best understood with reference to the cross-sectional view of FIG. 12a, the first "cryostat" 310a includes a superconducting element for levitating the bearing in the form of an annular superconducting element 312a. The superconducting element 312a is suspended in a chamber 314a defined by the cryostat 310a, which may be evacuated or insulated to prevent thermal transfer to the pipe 304 or the passing fluid F. The cryostat 3 10a may include an inner wall adjacent to the outer surface of the pipe 304 (not shown), but such a wall is not necessary in view of the thermal separation afforded by the evacuated or insulated space surrounding the superconducting element 312a. The superconducting element 312a may be coupled to annular support platform 316a, which in turn is thermally linked to one or more separate cooling sources 318. The connection is only shown schematically in FIG. 12, but as should be appreciated from reviewing the foregoing disclosure, may include a rod that serves to thermally link a container holding a liquid cryogen or a closed cycle refrigerator to the superconducting element 312a. While not shown in detail, "cryostat" 310b may be identical to the cryostat 310a just described.

With reference now to FIGS. 12b and 12c, two different motive devices for rotating the magnetic bearing 302 in the pipe 304 are disclosed. The first motive device includes a driving magnet assembly 320 that is rotatably supported on a bearing 322, such as a mechanical ball or roller bearing, carried on the outer surface of the pipe 304. The magnet assembly 320 includes a plurality of driving magnets 320a . . . 320n, also having different or alternating polarities. As with the driven magnets 308a . . . 308n, the driving magnets 320a . . . 320n are embedded or attached to an inert, non-magnetic matrix material M, such as plastic. An endless belt 324 also forming a part of the motive device frictionally engages both the driving magnet assembly 320 and a pulley W carried on the spindle or shaft of a motor (preferably a reversible, variable speed electric motor, as described above).

As should now be appreciated, the bearing 302 is caused to levitate in the pipe 304 as a result of the interaction of the levitation magnets 305a, 305b with the adjacent superconducting elements 312a, 312b, which may be thermally separated from the outer surface of the pipe 304 (or the adjacent inner wall of the cryostat 310a, 310b, if present). Upon then rotating the magnetic drive assembly 320, the bearing 302 is caused to rotate in the pipe 304 serving as the vessel to provide the desiring pumping or mixing action. Even if the fluid F is flowing past the magnetic bearing 302, it remains held in place in the desired position in the pipe 304 as a result of the pinning forces created by the superconducting elements 312a, 312b, acting on the levitation magnets 305a, 305b.

The second version of a motive device is shown in the cross-sectional view of FIG. 12c, which is similar to the cross-section taken in FIG. 12b. However, instead of a magnetic driving assembly 320, endless belt 324, and motor, rotary motion is imparted to the magnetic bearing 302 by creating an electrical field around the pipe 304. This may be done by placing a winding 326 around the outer wall of the pipe 304 and supplying it with an electrical current, such as from a power supply 328 or other source of AC current. Since the bearing 302 carries magnets 308a . . . 308n having different polarities, the resulting electric field will thus cause it to rotate.

Yet another embodiment of an inline pumping or mixing system 400 is shown in FIG. 13. The cryostat 402 in this case is essentially positioned directly in the path of fluid flow along the pipe 403, thus creating an annular (or possibly upper and lower) flow channels 404a, 404b. The cryostat 402 has an outer wall 406 that defines a chamber 408 for containing a superconducting element 410. The superconducting element 410 may be annular in shape, in which case the chamber 408 is of a similar shape. The chamber 408 may also be evacuated or insulated to thermally separate the superconducting element 410 from the outer wall 406. The superconducting element 410 is thermally linked to a separate cooling source 412, with both the thermal link and the cooling source being shown schematically in FIG. 13. It should be appreciated that this cryostat 402 is similar in many respects to the one described above in discussing the third embodiment illustrated in FIG. 9, which employs a similar, but somewhat reoriented, arrangement.

The wall 406 creating annular chamber 408 for the superconducting element 410 defines a room temperature bore or opening 414 into which a portion of a motive device may be inserted, such as the end of a shaft 416 carrying at least two driving magnets. FIG. 13 illustrates the motive device with three such driving magnets 418a, 418b, 418c, one of which is aligned with the rotational axis of the shaft 416. The opposite end of the shaft 416 is coupled to a motor (not numbered), which rotates the shaft and, hence, the driving magnets 418a, 418b, and 418c. The magnets 418a, 418b, 418c may be coupled directly to the shaft 416, or embedded/attached to an inert matrix material M.

The magnetic bearing 420 is positioned in the pipe 403 adjacent to the outer wall 406 of the cryostat 402. The bearing 420 includes a levitation magnet 422 that corresponds in size and shape to the superconducting element 410, as well as driven magnets 424a, 424b, 424c that correspond to the driving magnets 418a, 418b, and 418c. The levitation magnet 422 and driven magnets 424a-424c are attached to or embedded in a matrix material M, which may also support one or more blades B that provide the desired pumping or mixing action.

In operation, the motor rotates the shaft 416 to transmit rotary motion to the driving magnets 418a, 418b and 418c. As a result of the magnetic coupling formed between these magnets 418a-c and the opposite polarity driven magnets 424a-c, the bearing 420 is caused to rotate in the fluid F. At the same time, the bearing 420 remains magnetically suspended in the fluid F as the result of the pinning forces created between the superconducting element 410 and the levitation magnet 422. The operation is substantially the same as that described above with regard to the third embodiment, and thus will not be explained further here.

Figure 14:
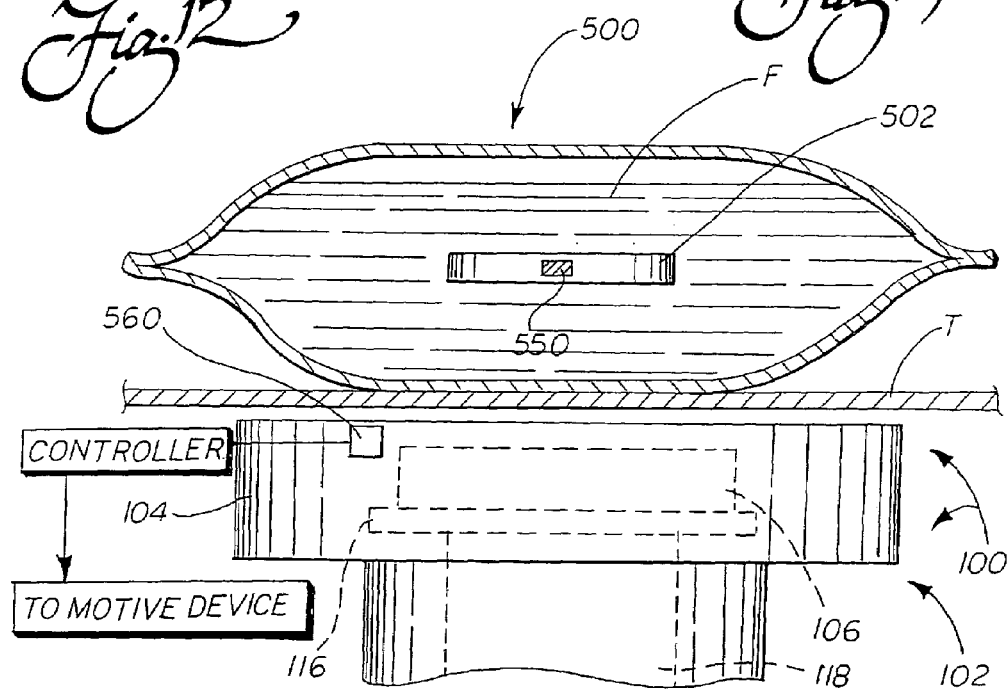
FIG. 14 is an enlarged partially cross-sectional, partially cutaway side view showing the manner in which a sealed flexible bag carrying a magnetic bearing may be used for mixing a fluid, and also showing one example of how a transmitter and receiver may be used to ensure that the proper bearing is used with the system.

Various optional modifications may in some circumstances enhance the set-up or performance of any of the systems described above, or instead adapt them for a particular use, purpose, or application. As noted previously, the disposable vessel or container for holding the fluid undergoing pumping or mixing may be in the form of a flexible bag. An example of such a bag 500 is shown in FIG. 14, along with the system 100 for levitating the bearing 502 of FIG. 5. The bag 500 may be sealed with the fluid F and bearing 502 (which may take the form of one of the several bearings disclosed above or an equivalent thereof) inside prior to distribution for use, or may be provided with a sealable (or resealable) opening that allows for the fluid and bearing to be introduced and later retrieved.

Both the bearing and bag 500, whether permanently sealed or resealable, may be fabricated of inexpensive, disposable materials, such as plastics. Accordingly, both can simply be discarded after the pumping or mixing operation is completed and the fluid F is retrieved. It should also be appreciated that the vertical dimension of the bag 500 is defined by the volume of fluid F held therein. Thus, instead of placing the bag 500 containing the bearing 502 directly on the surface of the cryostat, table T, or other support structure adjacent to the superconducting element 106, it is possible to place the flexible bag 500 in a separate rigid or semi-rigid container (not shown). This helps to ensure that the fluid F provides the bag 500 with a sufficient vertical dimension to permit the bearing to freely rotate in a non-contact fashion. Alternatively, the bag 502 may include internal or external reinforcements (not shown) to enhance its rigidity without interfering with the rotation of the magnetic bearing.

Figure 14A:
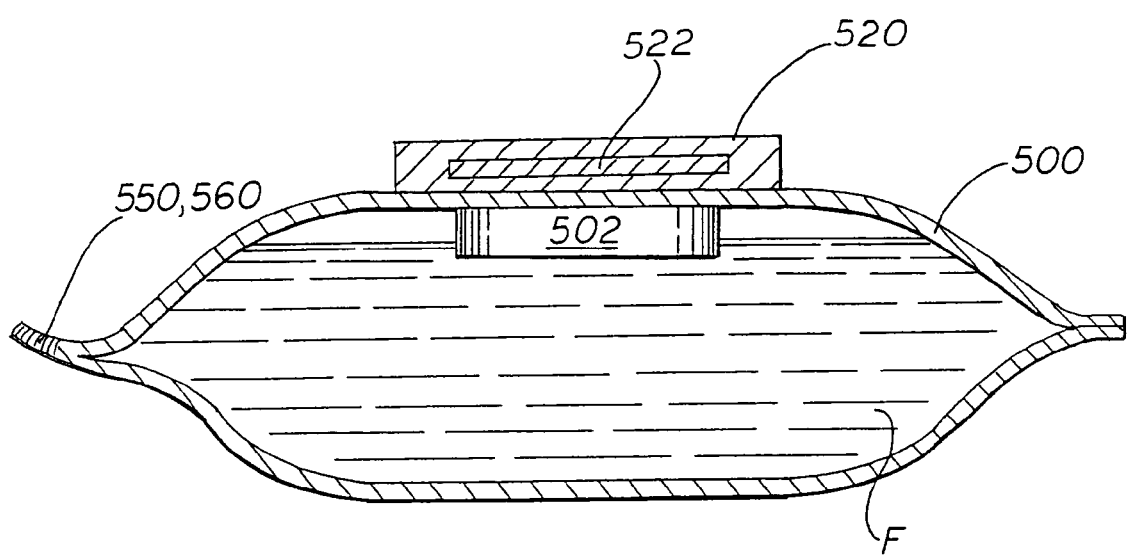
FIG. 14a is an enlarged, partially cross-sectional, partially cutaway side view showing an attachment including a coupler for coupling with the magnetic bearing.

In cases where the bearing 502 is prepackaged in the bag 500, with or without fluid, it may inadvertently couple to adjacent magnets or other metallic structures. Breaking this coupling may render the bag susceptible to puncturing, tearing, or other forms of damage. Accordingly, as shown in FIG. 14a, it may be desirable to place an attachment 520, cover, or similar device including a coupler 522 formed of a ferromagnetic material or the like adjacent to the bag 500, especially in cases where it is sealed with the bearing 502 inside during manufacturing. This coupler 522 is thus attracted to and forms a magnetic coupling with the magnetic bearing 502 when the attachment 520 is in place. As a result of this coupling, the magnetic bearing 502 is prevented from coupling with magnets in adjacent bags or other magnetic structures (not shown). The attachment 520 should be fabricated of a non-magnetic material, such as rubber. The coupler 522 will shield the magnetic field created by the bearing 502. When the assembly including the bag 500 and the bearing 502 is ready for use, the attachment 520 may simply be removed from the bag 500 to break the magnetic coupling between the bearing 502 and the coupler 522.

In all of the above-described embodiments, the pumping or mixing action is essentially localized in nature. This may be undesirable in some situations, such as where the vessel is relatively large compared to the magnetic bearing. To solve this problem, the particular system used to supply the pumping or mixing action may be provided with a motive device for physically moving the superconducting element (which may also be simultaneously rotated), which will cause the levitating magnetic bearing to follow a similar path.

With reference to the schematic view of FIG. 14b, and by way of example only, the particular arrangement is shown in use on the system 100 of FIG. 5, but with the bag 500 of FIG. 14. In addition to a motive device 540 for rotating the first portion of the cryostat 102a (which may comprise the bearing(s) 120, endless belt 128, motor 131, shaft, and pulley) and a cooling source 541, the system 100 may include a second motive device 542. In one embodiment, this second motive device 542 (shown schematically in dashed line outline only in FIG. 14b) is capable of moving the first portion of the cryostat 102a, and hence the superconducting element 106, to and fro in a linear fashion (see action arrows L in FIG. 14b). Thus, in addition to levitating and rotating the bearing 502, the side-to-side motion allows it to move relative to the bag 500 or other vessel containing the fluid. This advantageously permits non-localized pumping or mixing action to be provided. The motive device 542 may include a support structure, such as a platform (not shown) for supporting all necessary components, such as the first portion of the cryostat 102a (or the entire cryostat, such as in the embodiment of FIG. 9), the first motive device 540 for rotating one of the superconducting element 106 (or the magnetic bearing 502 such as in the embodiment of FIG. 9), and the cooling source 541 (which may form part of the cryostat as shown in FIG. 9, or may be a separate component altogether, as shown in FIG. 2). Instead of using a linear motion device, it should also be appreciated that the second motive device 542 may be capable of moving the superconducting element in a circular or elliptical pattern relative to the fixed position of the bag 500 or other vessel, or in any other direction that will enhance the overall mixing or pumping action provided by the rotating magnetic bearing 502. Also, the bag 502 or vessel may be separately rotated or moved to further enhance the operation (see the above-description of the embodiment of FIG. 3).

Ensuring that the magnetic bearings used in each system are both proper for that particular system and are sized properly may also be important. To do so, it is possible to provide a transmitter in one of the magnetic bearing or the vessel for generating a signal that is received by a receiver in the system (or vice versa), such as one positioned adjacent to the superconducting element or elsewhere. An example of one possible configuration is shown in FIG. 14, wherein the transmitter 550 is provided on the bearing 502 itself and the receiver 560 is positioned in the cryostat 102 (but see FIG. 14a, wherein the transmitter 550 or receiver 560 is provided in the bag serving as the vessel). A controller for the system, such as a computer (not shown) or other logic device, can then be used to maintain the system for rotating the bearing 502 in a non-operational, or "lock-out," condition until the receiver and transmitter 550, 560 correspond to each other (that is, until the transmitter 550 generates an appropriate signal that is received by the receiver 560). The transmitter/receiver combination employed may be of any type well known in the art, including electromagnetic, ultrasound, optical, or any other wireless or remote signal transmitting and receiving devices.

In accordance with another aspect of the invention, a kit is also provided to assist in the set-up of any of the systems previously described. Specifically, and as briefly noted in both this and my prior pending application, it is necessary during field cooling to cool the superconducting element to below its transition temperature in the presence of a magnetic field in order to induce levitation in a permanent magnet producing the same magnetic field. This cooling process causes the superconducting element to "remember" the field, and thus induce the desired levitation in the bearing each time it or an additional magnet is placed over the superconducting element. While it is possible to use the magnetic bearing itself to produce the magnetic field during field cooling, oftentimes the bearing will be sealed in the vessel or container. This makes it difficult, if not impossible, to ensure that the magnet is properly aligned and spaced from the superconducting element during cooling.

Figure 15:
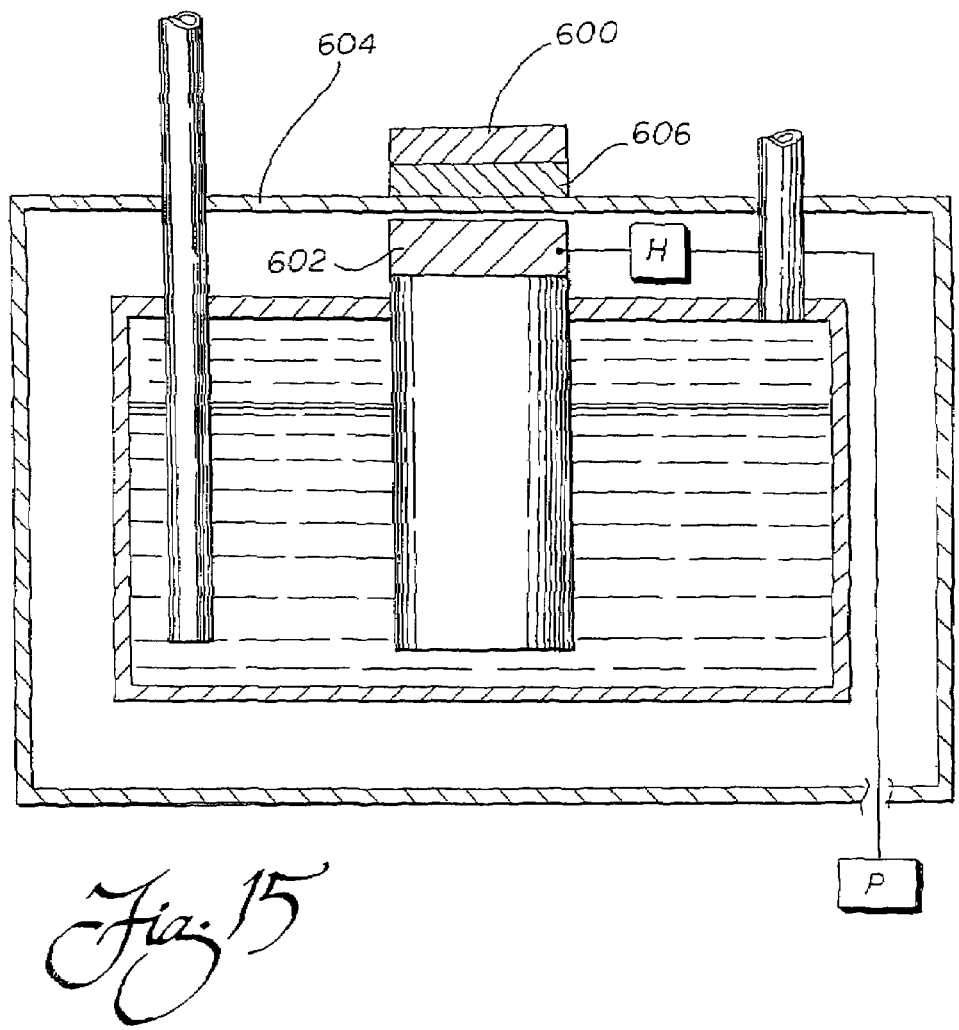
FIG. 15 illustrates one charging magnet including a spacer that may form part of a kit for use in charging the superconducting element as it is cooled to the transition temperature, as well as a heater for warming the superconducting element to above the transition temperature for recharging.

To overcome this potential problem, the set-up kit of the present invention as illustrated in FIG. 15 comprises a charging magnet 600 having a size, shape, and magnetic field distribution that is identical to the levitation magnet contained in the particular bearing slated for use in one of the pumping or mixing systems previously described. The charging magnet 600 is placed adjacent to the superconducting element 602, such as on the upper surface of the cryostat 604, table (not shown), or other chamber. As illustrated, the charging magnet 600 may further include a spacer 606. This spacer 606 allows the charging magnet 600 to simulate the spacing of the magnetic bearing (not shown) above the superconducting element 602 during field cooling. This ensures that the desired levitation height is achieved for the magnetic bearing (not shown) once the vessel is in position. The spacer 606 is formed of a non-magnetic material to avoid interfering with the charging process. By providing a variety of different sizes, shapes, and configurations of charging magnets in the kit (e.g., annular magnets), it is possible to easily perform field cooling for any corresponding size or shape of levitation magnet in the corresponding magnetic bearing, and then simply place the vessel containing the bearing over the superconducting element 602 to induce the desired stable, reliable levitation.

During field cooling, and regardless of whether the magnetic bearing or a separate charging magnet 600 is used to produce the charging magnetic field, it is possible to induce an undesired magnetic state in the superconducting element 602, such as if the position of the bearing (not shown) or charging magnet 600 is not correct. Since improper charging may prevent the magnetic bearing from levitating in a stable fashion, recharging the superconducting element 602 may be required. To facilitate recharging the superconducting element, it is provided with a heater H, such as an electric heating coil (not shown). By energizing this coil using a power supply P or other source of electrical current (not shown), the superconducting element 602 may be quickly brought up from the transition temperature for recharging. As shown schematically, the power supply P is preferably positioned externally to the cryostat 604. Once the position of the bearing or charging magnet 600 is adjusted or corrected, the heater H may be turned off and the superconducting element once again allowed to cool to the transition temperature in the presence of the desired magnetic field.

In summary, a number of systems 10, 100, 200, 300, as well as variations on these systems and related methods, are disclosed that use or facilitate the use of superconducting technology to levitate a bearing that, when rotated, serves to pump or mix a fluid. In one system 10, the magnetic bearing 14 is placed in a fluid vessel 16 positioned external to a cryostat 12 having an outer wall or other housing 18 for containing a superconducting element 20. A separate cooling source 24 (either a cryogenic chamber 26, FIGS. 1 and 3 or a refrigerator 48, FIG. 2) thermally linked to the superconducting element 20 provides the necessary cooling to create the desired superconductive effects and induce levitation in the magnetic bearing 14. Since the bearing levitates in the fluid F, no penetration of the vessel walls by mixing or stirring rods is necessary, which eliminates the need for dynamic bearings or seals.

Additionally, the outer wall 18 of the cryostat 12 or other housing defines a chamber 25 that thermally isolates and separates the superconducting element 20 from the vessel 16 containing the fluid F and magnetic bearing 14. The thermal isolation may be provided by evacuating the chamber 25, or filling it with an insulating material. By virtue of this thermal isolation and separation, the superconducting element 20 can be positioned in close proximity to the outer wall or housing 18 adjacent to the vessel 16 and magnetic bearing 14, thereby achieving a significant reduction in the separation distance between the magnetic bearing 14 and the superconducting element 20. This enhances the magnetic stiffness and loading capacity of the magnetic levitating bearing 14, thus making it suitable for use with viscous fluids or relatively large volumes of fluid.

The exceptionally stable levitation provided as a result of the reduced separation distance also significantly reduces the potential for contact between the rotating bearing and the bottom or sidewalls of the vessel. This makes this arrangement particularly well-suited for use in fluids that are sensitive to shear stress or the effects of frictional heating. However, since the superconducting element 20 is substantially thermally isolated and separated from the vessel 16, the magnetic bearing 14, and hence the fluid F contained therein, may be shielded from the cold temperatures generated by the cooling source 24 to produce the desired superconductive effects and the resultant levitation. This allows for temperature sensitive fluids to be mixed or pumped. By using means external to the vessel 16 to rotate and/or stabilize the magnetic bearing 14 levitating in the fluid F, such as one or more rotating driving magnets coupled to the magnetic bearing 14, the desired pumping or mixing action is provided.

Additional embodiments of systems 100, 200 for pumping or mixing a fluid wherein the necessary motive force is provided from the same side of the vessel at which the superconducting element is positioned are also disclosed, as are systems 300, 400 for rotating an inline magnetic bearing positioned in a vessel in the form of a pipe or the like.

The foregoing description of various embodiments of the present invention have been presented for purposes of illustration and description. The description is not intended to be exhaustive or to limit the invention to the precise forms disclosed. Obvious modifications or variations are possible in light of the above teachings. The embodiments described provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. An assembly for intended use in association with a system for pumping or mixing a fluid using a magnet forming part of a magnetic bearing and associated with a motive device without the need for any shaft or seal connected to the magnet, comprising:
   a flexible bag including the magnet supporting at least one blade or vane; and
   an attachment supported by the bag, the attachment comprising a coupler for forming a coupling with the magnet through the bag.

2. The assembly of claim 1, wherein the coupler comprises a ferromagnetic material.

3. The assembly of claim 1, wherein the coupling is a magnetic coupling.

4. The assembly of claim 1, wherein the attachment further comprises a non-magnetic material.

5. The assembly of claim 4, wherein the non-magnetic material is elastic.

6. The assembly of claim 4, wherein the non-magnetic material is sandwiched between the coupler and the bag.

7. The assembly of claim 4, wherein the non-magnetic material surrounds the coupler.

8. The assembly of claim 1, wherein the bag is sealed with the magnet inside.

9. In an assembly for mixing a fluid using a magnet positioned in a flexible bag and having a magnetic field for forming part of a magnetic bearing with a motive device external to the bag, the improvement comprising an attachment carried by the bag, the attachment including a coupler for coupling with the magnet and thereby shielding the magnetic field, wherein the magnet supports at least one blade or vane.

10. The assembly of claim 9, wherein the coupler comprises a ferromagnetic material.

11. The assembly of claim 9, wherein the coupling is a magnetic coupling.

12. The assembly of claim 9, wherein the attachment further comprises a non-magnetic material.

13. The assembly of claim 9, wherein the bag is sealed with the magnet inside.

14. A method of pumping or mixing a fluid using a magnet positioned in a bag and forming a magnetic bearing with an external motive device, comprising:
   at least partially filling the bag with the fluid;
   breaking a coupling between a coupler carried by the bag and the magnet; and
   after the breaking step, using the magnet to agitate the fluid.

15. The method of claim 14, wherein the using step comprises rotating the magnet using the motive device.

16. An assembly for use in association with a system for pumping or mixing a fluid, comprising:
   a flexible plastic bag including an external surface and an interior compartment capable of holding the fluid;
   a magnetic impeller for agitating the fluid positioned within the interior compartment of the bag; and
   an attachment carried by the bag adjacent to the external surface, the attachment comprising a coupler for forming a coupling with the magnetic impeller.

17. The assembly of claim 16, wherein the magnetic impeller includes a first magnet, and the coupler includes a second magnet for coupling with the first magnet.

18. The assembly of claim 17, wherein the bag and at least two layers of non-magnetic material are sandwiched between the magnets.

19. The assembly of claim 18, wherein at least one of the layers of non-magnetic material touches one of the magnets.

20. The assembly of claim 16, wherein the impeller further includes at least one blade or vane.

* * * * *